US012727770B2

(12) United States Patent
Kim

(10) Patent No.: US 12,727,770 B2
(45) Date of Patent: Sep. 8, 2026

(54) ELECTRONIC DEVICE INCLUDING A BLOOD PRESSURE SENSOR

(71) Applicant: SAMSUNG DISPLAY CO., LTD., Yongin-si (KR)

(72) Inventor: Chul Kim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 288 days.

(21) Appl. No.: 18/152,738

(22) Filed: Jan. 10, 2023

(65) Prior Publication Data

US 2023/0389810 A1 Dec. 7, 2023

(30) Foreign Application Priority Data

Jun. 7, 2022 (KR) ........................ 10-2022-0068749

(51) Int. Cl.
*A61B 5/021* (2006.01)
*A61B 5/00* (2006.01)

(52) U.S. Cl.
CPC .......... *A61B 5/02108* (2013.01); *A61B 5/681* (2013.01); *A61B 2562/0247* (2013.01)

(58) Field of Classification Search
CPC ..... A61B 5/021; A61B 5/02416; A61B 5/681; A61B 5/02108; A61B 5/6831
See application file for complete search history.

(56) References Cited

U.S. PATENT DOCUMENTS

| | | | | |
|---|---|---|---|---|
| 10,398,324 B2 | 9/2019 | Mukkamala et al. | | |
| 2008/0183053 A1* | 7/2008 | Borgos | A61B 5/02007 600/301 | |
| 2017/0042433 A1* | 2/2017 | Noh | A61B 5/02108 | |
| 2018/0192946 A1* | 7/2018 | Adachi | A61B 5/022 | |
| 2019/0008399 A1* | 1/2019 | Mukkamala | A61B 5/0261 | |
| 2019/0110699 A1* | 4/2019 | Quinn | A61B 5/6824 | |

FOREIGN PATENT DOCUMENTS

| | | |
|---|---|---|
| JP | 4795731 | 10/2011 |
| KR | 10-2009-0052442 | 5/2009 |
| KR | 10-20210012421 | 2/2021 |

* cited by examiner

*Primary Examiner* — Anh Tuan T Nguyen
*Assistant Examiner* — Younhee Choi
(74) *Attorney, Agent, or Firm* — F. CHAU & ASSOCIATES, LLC

(57) ABSTRACT

An electronic device includes a display unit, a pressure sensor unit, a blood pressure sensor unit, and a driving unit. The driving unit includes a first calculator configured to calculate a first blood pressure based on a pressure signal received from the pressure sensor unit and a first pulse wave signal received from the blood pressure sensor unit in a first blood pressure measurement mode, and a second calculator configured to calculate a second blood pressure by comparing a second pulse wave signal received from the blood pressure sensor unit in a second blood pressure measurement mode with the first pulse wave signal received in the first blood pressure measurement mode.

15 Claims, 29 Drawing Sheets

ELECTRONIC DEVICE INCLUDING A BLOOD PRESSURE SENSOR

This application claims priority under 35 U.S.C. § 119 to Korean Patent Application No. 10-2022-0068749, filed on Jun. 7, 2022 in the Korean Intellectual Property Office, the disclosure of which is herein incorporated by reference in its entirety.

TECHNICAL FIELD

The present disclosure relates to an electronic device, and more particularly, to an electronic device having a blood pressure sensor.

DISCUSSION OF THE RELATED ART

Electronic devices including display screens are applied not only to televisions and computer monitors but also to portable smartphones, smart watches, and tablet computers. A portable electronic device may have functions such as a camera and a fingerprint sensor in addition to a display function.

With the recent spotlight on the healthcare industry, methods of obtaining biometric information about health more easily are being developed. For example, attempts are being made to change a conventional oscillometric blood pressure measurement device into a portable electronic device. However, the electronic blood pressure measurement device itself requires an independent light source, a sensor, and a display and must generally be carried around separately from other devices that people tend to carry and wear.

SUMMARY

An electronic device includes a display unit; a pressure sensor unit; a blood pressure sensor unit; and a driving unit. The driving unit includes a first calculator configured to calculate a first blood pressure based on a pressure signal received from the pressure sensor unit and a first pulse wave signal received from the blood pressure sensor unit in a first blood pressure measurement mode; and a second calculator configured to calculate a second blood pressure by comparing a second pulse wave signal received from the blood pressure sensor unit in a second blood pressure measurement mode with the first pulse wave signal received in the first blood pressure measurement mode.

The second calculator may calculate the second blood pressure without the pressure signal received from the pressure sensor unit.

The second calculator may determine the second blood pressure by comparing the first pulse wave signal and the second pulse wave signal in terms of at least one of period, amplitude, area, feature points, and quadratic differential function graph.

The first pulse wave signal and the second pulse wave signal may be pulse wave signals for a same body part of a same person.

A part of a user's body may contact and apply pressure to the electronic device for a first measurement time in the first blood pressure measurement mode and may contact the electronic device for a second measurement time in the second blood pressure measurement mode.

The first measurement time may be in a range of 5 to 80 seconds, and the second measurement time may be less than or equal to the first measurement time.

The first blood pressure may be a reference blood pressure, and the second blood pressure may be a monitoring blood pressure.

The blood pressure sensor unit may include a light source and a photodetector.

The display unit may display an image upward, and the light source and the photodetector may be placed to face downward.

The electronic device may further include a housing accommodating the display unit, the pressure sensor unit, and the blood pressure sensor unit. The blood pressure sensor unit may be disposed under the display unit. The housing includes a light transmitting portion configured to transmit examination light emitted from the light source and reflected from an object.

The electronic device may further include a housing accommodating the display unit and the pressure sensor unit. The blood pressure sensor unit may be disposed on a bottom surface of a bottom portion of the housing.

The display unit may display an image upwardly, the blood pressure sensor unit may be disposed under the display unit, and the light source and the photodetector may be placed to face upwardly.

The display unit may include an optical hole at least partially overlapping each of the light source and the photodetector.

The display unit may include a light emitting pixel including a light emitting layer which emits examination light of the blood pressure sensor unit.

The display unit may further include a light receiving pixel including a photoelectric conversion layer which receives the examination light.

The driving unit may further include a memory storing the first pulse wave signal received from the blood pressure sensor unit in the first blood pressure measurement mode as a reference pulse wave signal.

An electronic device includes a display panel; a touch sensor disposed on the display panel; a protective member disposed on the touch sensor; a pressure sensor disposed on or under the display panel; a blood pressure sensor disposed under the display panel; and a housing accommodating the display panel, the touch sensor, the pressure sensor, and the blood pressure sensor. The display panel displays an image upwardly, the housing includes a bottom portion and a sidewall portion. The bottom portion includes a transmitting portion at least partially overlapping the blood pressure sensor.

The electronic device may further include a driving chip configured to calculate a first blood pressure based on a pressure signal received from the pressure sensor unit and a first pulse wave signal received from the blood pressure sensor unit in a first blood pressure measurement mode and calculate a second blood pressure by comparing a second pulse wave signal received from the blood pressure sensor unit in a second blood pressure measurement mode with the first pulse wave signal received in the first blood pressure measurement mode without using the pressure signal received from the pressure sensor unit.

A part of a user's body may contact and apply pressure to the electronic device for a first measurement time in the first blood pressure measurement mode and may contact the electronic device for a second measurement time in the second blood pressure measurement mode.

The electronic device may be a smart watch.

BRIEF DESCRIPTION OF THE DRAWINGS

These and/or other aspects of the present disclosure will become apparent and more readily appreciated from the following description of embodiments, taken in conjunction with the accompanying drawings, in which.

DETAILED DESCRIPTION

Figure 1:
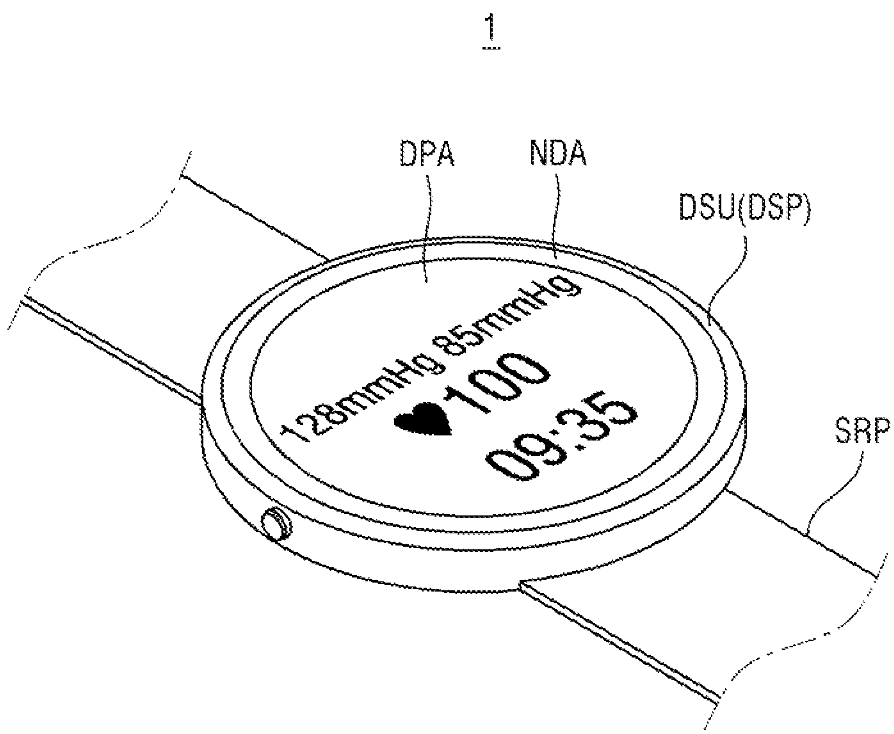
FIG. 1 is a schematic perspective view of an electronic device according to an embodiment of the present disclosure.

Embodiments of the invention will now be described more fully hereinafter with reference to the accompanying drawings, in which embodiments of the invention are shown. The invention may, however, be embodied in different forms and should not necessarily be construed as limited to the embodiments set forth herein. The same reference numbers may indicate the same components throughout the specification and the drawings. While the attached drawing may be drawn to scale to represent at least one embodiment of the present invention, the present invention is not necessarily limited to the thickness of layers and regions illustrated in the figures.

It will be understood that, although the terms "first," "second," "third" etc. may be used herein to describe various elements, components, regions, layers and/or sections, these elements, components, regions, layers and/or sections should not necessarily be limited by these terms. These terms are used to distinguish one element, component, region, layer or section from another element, component, region, layer or section. Thus, "a first element," "component," "region," "layer" or "section" discussed below could be termed a second element, component, region, layer or section without departing from the teachings herein.

It will also be understood that when a layer is referred to as being "on" another layer or substrate, it can be directly on the other layer or substrate, or intervening layers may also be present. In contrast, when an element is referred to as being "directly on" another element, there are no intervening elements present.

As used herein, the singular forms "a," "an," and "the" are intended to include the plural forms, including "at least one," unless the content clearly indicates otherwise. "Or" means "and/or." "At least one of A and B" means "A and/or B." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system).

It is to be understood that variations from the shapes of the illustrations as a result, for example, of manufacturing techniques and/or tolerances, may be present. Thus, embodiments described herein should not necessarily be construed as limited to the particular shapes of regions as illustrated herein but are to include deviations in shapes that result, for example, from manufacturing. For example, a region illustrated or described as flat may have rough and/or nonlinear features. Moreover, sharp angles that are illustrated may be rounded.

Figure 2:
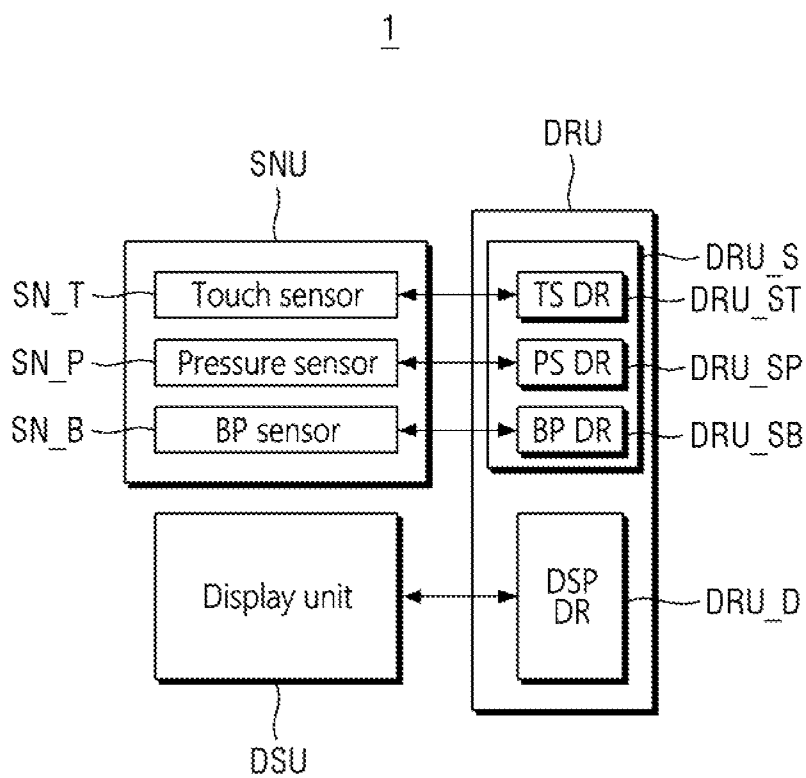
FIG. 2 is a block diagram of the electronic device of FIG. 1.

FIG. 1 is a schematic perspective view of an electronic device 1 according to an embodiment of the present disclosure. FIG. 2 is a block diagram of the electronic device 1 of FIG. 1.

Referring to FIG. 1, the electronic device 1, according to an embodiment of the present disclosure includes a display unit DSU. The display unit DSU displays a moving image or a still image. The display unit DSU may include a display panel DSP. Although the electronic device 1 including the display unit DSU is a smart watch in FIG. 1, the present disclosure is not necessarily limited thereto. For example, applicable examples of the electronic device 1 include portable electronic devices such as various wearable electronic devices including a smart watch, a smartphone, a mobile phone, a tablet computer, a personal digital assistant (PDA), a portable multimedia player (PMP), a portable game machine, a laptop computer, a digital camera, and a camcorder. In addition to the portable electronic devices, fixed or mobile electronic devices including the display unit DSU, such as a computer monitor, a car navigation system, a car dashboard, an outdoor billboard, an electronic display board, various medical devices, various examination devices, a refrigerator, and washing machine may be included in the scope of application of embodiments where there is a desire to apply a blood pressure measurement module to them. The above-listed various electronic devices 1 including the display unit DSU may also be referred to as display devices.

The electronic device 1 of FIG. 1 may be worn on a body part of a user (or a subject). For example, the electronic device 1 may be configured to be worn on the wrist or ankle of the user/subject. To this end, the electronic device 1 may further include a strap SRP configured to fix the display unit DSU on a part of the user's body.

Referring to FIGS. 1 and 2, the electronic device 1 may further include a sensor unit SNU and a driving unit DRU in addition to the display unit DSU.

The sensor unit SNU may include a plurality of sensors. The sensor unit SNU may include a pressure sensor SN_P sensing the magnitude of applied pressure and a blood pressure sensor SN_B sensing the magnitude of blood pressure. The sensor unit SNU may further include a touch sensor SN_T sensing the presence or absence of a touch event input and coordinates. The sensor unit SNU may further include an infrared sensor, a luminance sensor, a fingerprint recognition sensor, an iris recognition sensor, and/or a temperature sensor.

The driving unit DRU may include a display driving unit DRU_D and a sensor driving unit DRU_S.

The display driving unit DRU_D may process image information that is externally received by the electronic device 1 or image information stored in the electronic device 1 and may drive the display unit DSU to display a corresponding image. In addition, the display driving unit DRU_D may process stored image information or generate and process new image information in response to a user's input and provide the image information to the display unit DSU. In addition, the display driving unit DRU_D may process stored or new image information based on information sensed by the sensor unit SNU and provide the image information to the display unit DSU. Further, the display driving unit DRU_D may correct an image processing signal using its own feedback circuit. The role of the display driving unit DRU_D is not necessarily limited to the above examples.

The sensor driving unit DRU_S may drive the operation of a sensor or process information sensed from the sensor. In embodiments, functions of a sensor and the sensor driving unit DRU_S are separately described for the sake of convenience. However, some functions performed by each sensor to be described below may also be performed by the sensor driving unit DRU_S.

The sensor driving unit DRU_S may be provided for each sensor. For example, the sensor driving unit DRU_S may include a pressure sensor driving unit DRU_SP, a blood pressure sensor driving unit DRU_SB, and a touch sensor driving unit DRU_ST.

The pressure sensor driving unit DRU_SP may transmit a driving signal to the pressure sensor SN_P to activate the pressure sensor SN_P and may receive information measured by the pressure sensor SN_P to calculate the magnitude of pressure.

The blood pressure sensor driving unit DRU_SB may transmit a driving signal to the blood pressure sensor SN_B to activate the blood pressure sensor SN_B and may calculate the magnitude of blood pressure based on information measured by the blood pressure sensor SN_B.

The touch sensor driving unit DRU_ST may transmit a driving signal to the touch sensor SN_T and calculate whether a touch event has occurred and calculate touch coordinates based on information sensed by the touch sensor SN_T.

The driving unit DRU may be provided in the form of a driving chip (e.g., an integrated circuit). Although each driving unit DRU may be provided in the form of an individual driving chip, a plurality of driving units DRU may also be integrated into one driving chip. In an embodiment of the present disclosure, the display unit DSU may include the display panel DSP, and the driving unit DRU may be mounted on the display panel DSP in the form of one or more driving chips.

Figure 3:
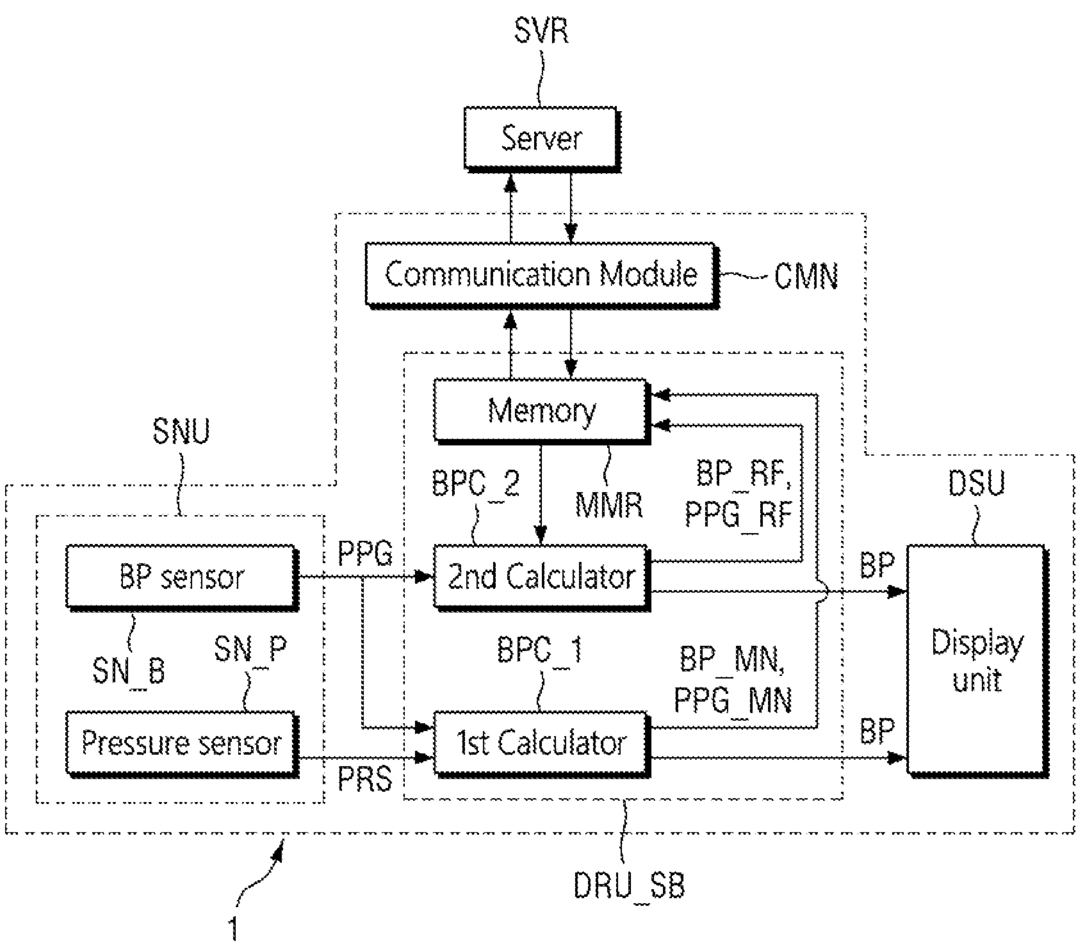
FIG. 3 is a block diagram of a blood pressure sensor driving unit of the electronic device according to an embodiment of the present disclosure.

FIG. 3 is a block diagram of the blood pressure sensor driving unit DRU_SB of the electronic device 1, according to an embodiment of the present disclosure.

Referring to FIG. 3, the blood pressure sensor driving unit DRU_SB may include a blood pressure calculating unit BPC and a memory MMR. The blood pressure calculating unit BPC may include a first calculator BPC_1 and a second calculator BPC_2. Each of the first and second calculators BPC_1 and BCP_2 may be instantiated as a separate calculator circuit or they may both be instantiated as a single calculator circuit.

The first calculator BPC_1 may receive a pulse wave signal PPG generated by the blood pressure sensor SN_B and a pressure signal PRS generated by the pressure sensor SN_P. The first calculator BPC_1 may calculate blood pressure BP based on the received pulse wave signal PPG and the received pressure signal PRS. The calculated blood pressure BP may be displayed through the display unit DSU. In addition, the calculated blood pressure BP and the pulse wave signal PPG corresponding to the calculated blood pressure BP may be stored in the memory MMR as reference blood pressure BP_RF and a reference pulse wave signal PPG_RF, respectively.

The second calculator BPC_2 may receive the pulse wave signal PPG generated by the blood pressure sensor SN_B. Unlike the first calculator BPC_1, the second calculator BPC_2 might not receive the pressure signal PRS generated by the pressure sensor SN_P. Instead, the second calculator BPC_2 may receive the reference pulse wave signal PPG_RF stored in the memory MMR and/or the reference blood pressure BP_RF corresponding to the reference pulse wave signal PPG_RF. The second calculator BPC_2 may compare the received pulse wave signal PPG with the reference pulse wave signal PPG_RF and estimate and calculate current blood pressure BP from the reference blood pressure BP_RF based on a difference value between the received pulse wave signal PPG and the reference pulse wave signal PPG_RF. The calculated blood pressure BP may be displayed through the display unit DSU. In addition, the calculated blood pressure BP and the pulse wave signal PPG may be stored in the memory MMR as monitoring blood pressure BP_MN and a monitoring pulse wave signal PPG_MN.

The electronic device 1 may further include a communication module CMM. The communication module CMM may be configured to communicate data with at least one external electronic device, for example, a server SVR. The reference blood pressure BP_RF and the monitoring blood pressure BP_MN and/or the reference pulse wave signal PPG_RF and the monitoring pulse wave signal PPG_MN stored in the memory MMR may be transmitted to the server SVR through the communication module CMM. For example, they may be transmitted to a server of a hospital or emergency facility and used to analyze and monitor a user's health condition.

In addition, the communication module CMM may receive statistical blood pressure-pulse wave signal data from the external server SVR. The received statistical blood pressure-pulse wave signal data may be stored in the memory MMR. The memory MMR may provide the statistical blood pressure-pulse wave signal data to the second calculator BPC_2 and/or the first calculator BPC_1. The second calculator BPC_2 and/or the first calculator BPC_1 may correct the calculated blood pressure BP with reference to the statistical blood pressure-pulse wave signal data. The statistical blood pressure-pulse wave signal data may be stored in the memory MMR in advance.

The detailed operation of the blood pressure sensor driving unit DRU_SB will be described later.

Figure 4:
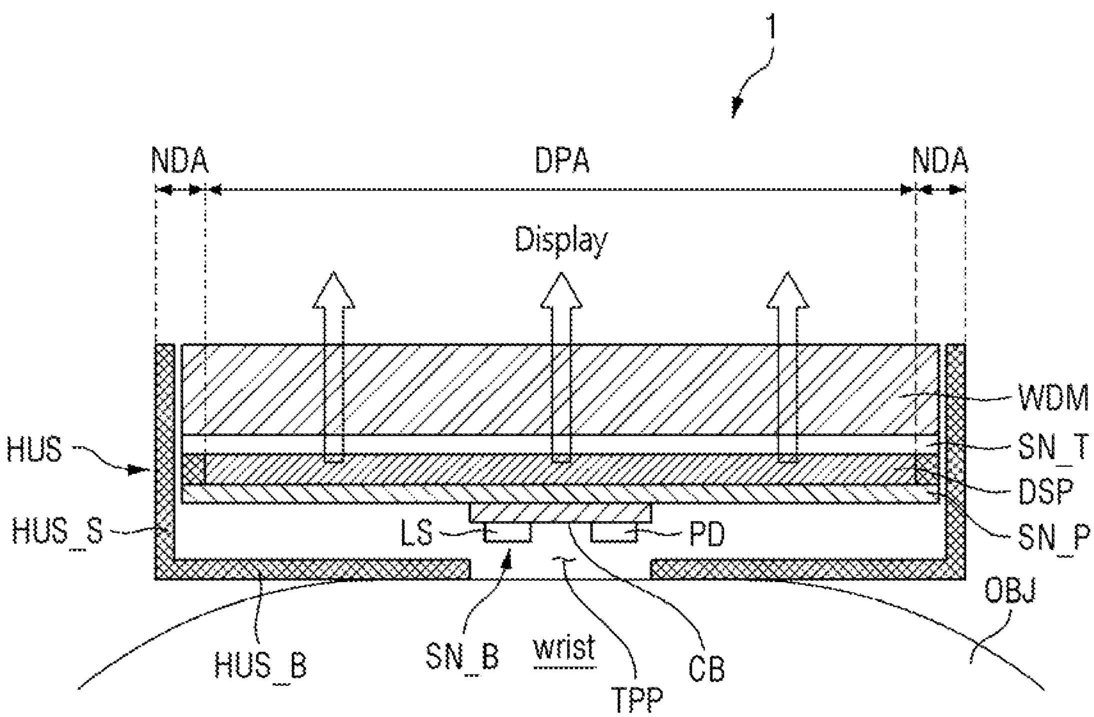
FIG. 4 is a schematic cross-sectional view of the electronic device of FIG. 1.

FIG. 4 is a schematic cross-sectional view of the electronic device 1 of FIG. 1.

Referring to FIGS. 1 and 4, the electronic device 1 may include the display panel DSP and a plurality of sensors. The display unit DSU described above may include the display panel DSP, and the sensor unit SNU may include a plurality of sensors. For example the display panel DSP is an implementation example of the display unit DSU, and the sensors are an implementation example of the sensor unit SNU. Furthermore, the electronic device 1 may further include a housing HUS for accommodating the display panel DSP and the sensors and a protective member WDM for protecting the display panel DSP, the protective member WDM being, for example, a window element.

The display panel DSP displays a moving image and/or a still image. Examples of the display panel DSP may include self-luminous display panels such as an organic light emitting display panel, an inorganic electroluminescent (EL) display panel, a quantum dot light emitting display panel (QED), a micro-light emitting diode (LED) display panel, a nano-LED display panel, a plasma display panel (PDP), a field emission display (FED) panel and a cathode ray tube (CRT) display panel as well as light-receiving display panels such as a liquid crystal display (LCD) panel and an electrophoretic display (EPD) panel. An organic light emitting display panel will be described below as an example of the display panel DSP. Unless a special distinction is required, the organic light emitting display panel applied to embodiments will be simply abbreviated as the display panel DSP. However, the embodiments are not necessarily limited to the organic light emitting display panel, and other display panels listed above or known in the art can also be applied within the scope sharing the technical spirit.

The display panel DSP displays an image by outputting light emitted from a light emitting layer. The display panel DSP includes a first surface (i.e., a front surface) and a second surface (i.e., a rear surface) opposite the first surface. The display panel DSP may be designed such that light emitted from the light emitting layer is output through the first surface and/or the second surface. In the drawing, the display panel DSP is illustrated as a top emission display panel that emits light through the first surface, for example, emits light upwardly. However, the present disclosure is not necessarily limited thereto, and a bottom emission display panel that emits light through the second surface or a double-sided emission display panel that emits light through both the first surface and the second surface is also applicable as the display panel DSP.

The planar shape of the display panel DSP may be a circular shape as illustrated in FIG. 1 or a shape including a part of the circular shape. However, the present disclosure is not necessarily limited thereto, and the planar shape of the display panel DSP may also be a polygonal shape such as a square, a rectangle, a hexagon, or an octagon. Alternatively, the planar shape of the display panel DSP may be a polygonal shape with inclined or curved corners.

The display panel DSP may include a display area DPA which displays an image and a non-display area NDA which does not display an image. The display area DPA may include a plurality of pixels PX (see FIG. 28). The non-display area NDA might not include the pixels PX or may include dummy pixels.

The non-display area NDA may be disposed along the periphery of the display panel DSP. In an embodiment of the present disclosure, the non-display area NDA may at least partially surround an outer surface of the display panel DSP in a closed curve shape. The non-display area NDA may be recognized as a bezel area.

In some embodiments, the non-display area NDA may also be disposed inside the display area DPA. For example, the non-display area NDA located around the display area DPA may be recessed into the display area DPA. As an example, an island-shaped non-display area NDA completely surrounded by the display area DPA may be further located inside the display area DPA.

The sensors may include the pressure sensor SN_P, the blood pressure sensor SN_B, and the touch sensor SN_T.

The pressure sensor SN_P senses the magnitude of input pressure. The pressure sensor SN_P may include, but is not necessarily limited to including, for example, a force sensor, a strain gauge, or a gap capacitor. Applicable pressure sensors SN_P will be described in detail later.

The pressure sensor SN_P may be configured to generate the pressure signal PRS corresponding to the magnitude of input pressure over time. To generate the pressure signal PRS, the pressure sensor SN_P may include a pressure signal generator. As an example, part or all of the pressure signal generator involved in the generation of the pressure signal PRS may be installed in the sensor driving unit DRU_S.

The pressure sensor SN_P may be disposed under the display panel DSP, for example, on the second surface of the display panel DSP. The pressure sensor SN_P may overlap the second surface of the display panel DSP in a thickness direction. The pressure sensor SN_P may overlap all or part of the second surface of the display panel DSP.

In an embodiment of the present disclosure, the pressure sensor SN_P may overlap the display area DPA of the display panel DSP. In an embodiment of the present disclosure, the pressure sensor SN_P may overlap the non-display area NDA of the display panel DSP. In some embodiments, the pressure sensor SN_P may overlap both the display area DPA and the non-display area NDA.

The pressure sensor SN_P may be attached on the second surface of the display panel DSP. In this case, an adhesive member may be interposed between the pressure sensor SN_P and the second surface of the display panel DSP.

The blood pressure sensor SN_B may include a photoplethysmogram sensor. The photoplethysmogram sensor (hereinafter, abbreviated as a 'pulse wave sensor') may include a photodetector PD that receives light reflected or scattered from an object OBJ. The photodetector PD may include, for example, a photodiode, a phototransistor, or a CMOS or CCD image sensor. The photoplethysmogram sensor may be configured to generate the pulse wave signal PPG by analyzing the amount of light received through the photodetector PD. To generate the pulse wave signal PPG, the photoplethysmogram sensor may include a pulse wave signal generator. As an example, part or all of the pulse wave signal generator involved in the generation of the pulse wave signal PPG may be installed in the sensor driving unit DRU_S.

The blood pressure sensor SN_B may further include a light source LS. The light source LS may provide examination light toward the object OBJ. As the wavelength of the examination light, an infrared wavelength, a visible wavelength, a red wavelength of visible light, a green wavelength of visible light, a blue wavelength of visible light, or the like may be applied. The light source LS may include at least one of, for example, an LED, an organic light emitting diode (OLED), a laser diode (LD), a quantum dot (QD), a phosphor, and natural light. In the drawing, an LED light source that emits infrared light is applied as the light source LS for providing the examination light. However, as will be described later, another light emitting source (e.g., the light emitting layer) provided in the electronic device may also be used (or may alternatively be used) as the light source LS.

The light source LS and the photodetector PD of the blood pressure sensor SN_B may be disposed under the display panel DSP. In addition, the light source LS and the photodetector PD may be disposed under the pressure sensor SN_P. For example the pressure sensor SN_P may be disposed between the display panel DSP and the blood pressure sensor SN_B.

The light source LS and the photodetector PD of the blood pressure sensor SN_B may be accommodated in the housing HUS while being mounted on a circuit board CB. The light source LS and the photodetector PD mounted on the circuit board CB may be collectively referred to as a blood pressure sensor module. The above members of the blood pressure sensor module may be disposed such that the circuit board CB faces upwardly, and the light source LS and the photodetector PD face downwardly in the housing HUS. In the above embodiment, an emission direction of the light source LS may be downward, and a light receiving element of the photodetector PD may face downwardly.

In an embodiment of the present disclosure, the circuit board CB on which the light source LS and the photodetector PD are mounted may be attached to a lower surface of the pressure sensor SN_P by an adhesive member or the like interposed between them. In some embodiments, the circuit board CB on which the light source LS and the photodetector PD are mounted may be attached to an inner surface of the housing HUS through an adhesive member or the like or may be fixed in the housing HUS through a mechanical coupling member such as a screw.

The touch sensor SN_T may be disposed on the display panel DSP, for example, on the first surface of the display panel DSP. The touch sensor SN_T may be referred to as a touch member.

The touch sensor SN_T may be formed integrally with the display panel DSP. For example, the touch sensor SN_T may be formed on an encapsulation layer covering light emitting elements of the display panel DSP. As an example, the touch sensor SN_T may be provided as a separate panel from the display panel DSP and may be attached onto the display panel DSP through a transparent bonding layer. As used herein, the term "transparent" means at least partially transparent to visible light.

The protective member WDM may be disposed on the touch sensor SN_T. The protective member WDM may include a transparent material. The protective member WDM may include, for example, glass, thin glass or ultra-thin glass, or a transparent polymer such as transparent polyimide. The protective member WDM may be referred to as a window or window member.

A transparent bonding layer for bonding the touch sensor SN_T and the protective member WDM may be disposed between them.

The housing HUS serves as a housing for accommodating the display panel DSP, the sensor unit SNU, the driving unit DRU, the protective member WDM, etc. The housing HUS may include a bottom portion HUS_B and a sidewall portion HUS_S extending in a vertical direction from the bottom portion HUS_B. The display panel DSP, the sensor unit SNU, the protective member WDM, etc. described above may be disposed in a space defined by the bottom portion HUS_B and the sidewall portion HUS_S.

A light transmitting portion TPP that can transmit examination light emitted from the light source LS of the blood pressure sensor SN_B and reflected from the object OBJ may be disposed in the bottom portion HUS_B of the housing HUS. For example, the bottom portion HUS_B of the housing HUS may generally be made of a material opaque to the examination light, for example, metal or opaque plastic, but the light transmitting portion TPP may include a physically penetrated opening through which the examination light can pass or may be made of a material that is transparent to the examination light.

The light transmitting portion TPP may completely overlap the light source LS and the photodetector PD of the blood pressure sensor SN_B in the thickness direction to expose them. However, the present disclosure is not necessarily limited thereto, and the light transmitting portion TPP might also not overlap part or all of the light source LS and the photodetector PD. For example, when the path of light emitted from the light source LS and the path of light reflected from the object OBJ are designed to be inclined with respect to the vertical direction, the positions of the light source LS and the photodetector PD may be at least partially covered by the bottom portion HUS_B other than the light transmitting portion TPP.

Figure 5:
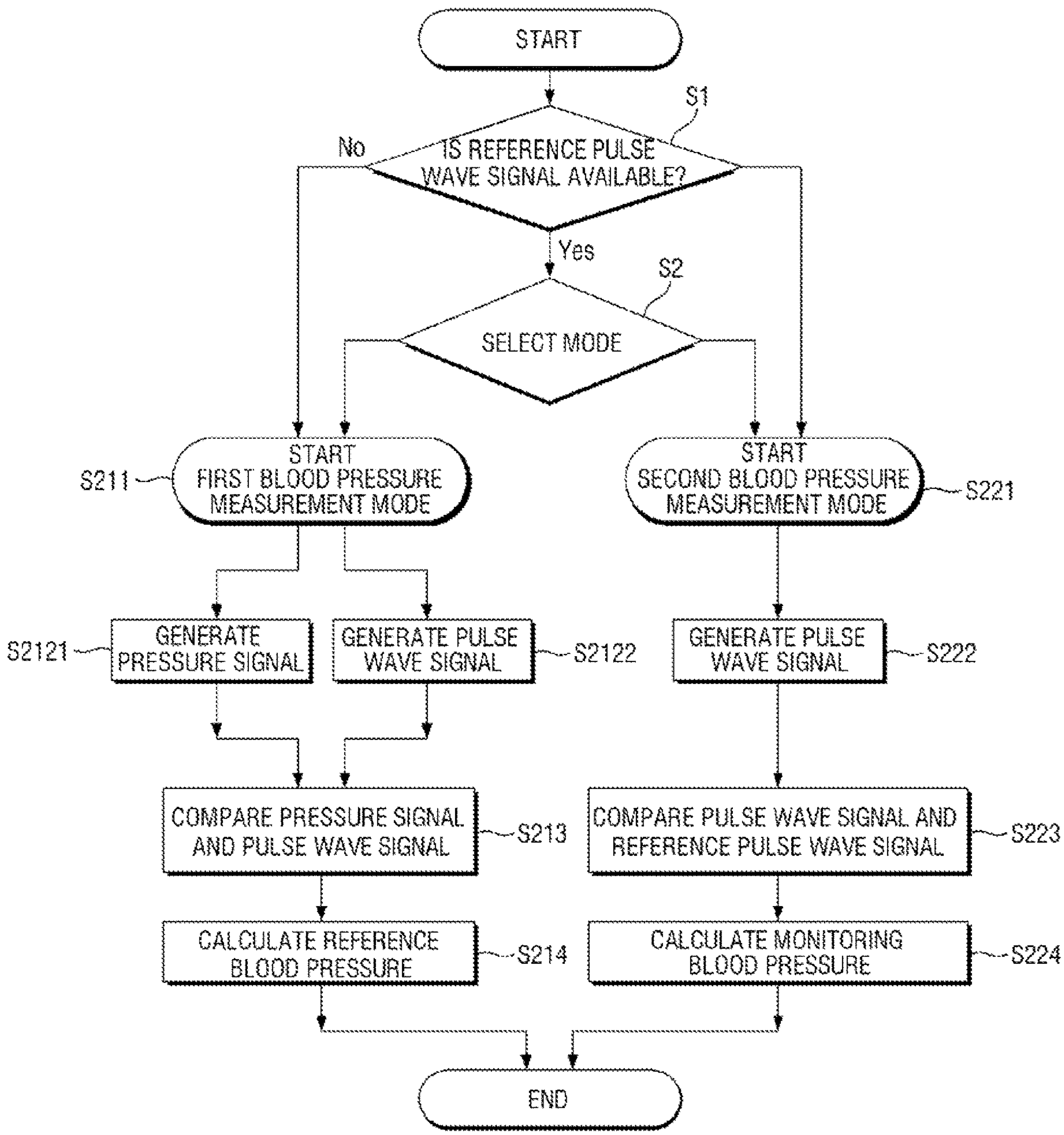
FIG. 5 is a flowchart illustrating the operation of the blood pressure sensor driving unit according to an embodiment of the present disclosure.

FIG. 5 is a flowchart illustrating the operation of the blood pressure sensor driving unit DRU_SB according to an embodiment of the present disclosure.

Referring to FIG. 5, the blood pressure sensor SN_B may operate in two modes. A first blood pressure measurement mode may be an absolute blood pressure measurement mode in which the blood pressure BP is measured using both the pressure signal PRS and the pulse wave signal PPG. A second blood pressure measurement mode may be a relative blood pressure measurement mode in which the blood pressure BP is measured using the pulse wave signal PPG and the reference pulse wave signal PPG_RF without the pressure signal PRS. The second blood pressure measurement mode may also be a monitoring blood pressure measurement mode suitable for real-time monitoring of the blood pressure BP. The second blood pressure measurement mode may be a ubiquitous/seamless blood pressure measurement mode.

First, it is determined whether there is an available reference pulse wave signal PPG_RF (operation S1). Since the second blood pressure measurement mode requires the reference pulse wave signal PPG_RF, when there is no available reference pulse wave signal PPG_RF, the first blood pressure measurement mode may be selected immediately.

The available reference pulse wave signal PPG_RF is a pulse wave signal calculated and stored through the first blood pressure measurement mode and may be the pulse wave signal PPG of the same user. In addition, even if the reference pulse wave signal PPG_RF of the same user is stored, when too long a time has elapsed from the generation of the reference pulse wave signal PPG_RF or when it is determined that a new reference pulse wave signal PPG_RF may be used in view of the user's age, medical history and blood pressure measurement environment, the first blood pressure measurement mode may be selected.

When there is an available reference pulse wave signal PPG_RF, the second blood pressure measurement mode may be immediately selected. However, the blood pressure measurement mode selection operation S2 may also be further performed. For example, when it is desired to update the user's reference pulse wave signal PPG_RF, the first blood pressure measurement mode may be selected despite the presence of the available reference pulse wave signal PPG_RF. In addition, the user may choose to enter the first blood pressure measurement mode as needed. In this way, a blood pressure measurement mode may be selected by the user's input or may be selected according to a programmed cycle.

When the first blood pressure measurement mode is selected (operation S211), the user may contact and apply pressure to the electronic device 1. For example contact and pressure application by a part of the user's body are input to the electronic device 1. The pressure sensor SN_P of the electronic device 1 may generate the pressure signal PRS corresponding to the pressure input (operation S2121), and the blood pressure sensor SN_B of the electronic device 1 may generate the pulse wave signal PPG from the contact of the user's body part (operation S2122). The generated pressure signal PRS and the generated pulse wave signal PPG may be transmitted to the first calculator BPC_1, and the first calculator BPC_1 may compare and process them (operation S213) and generate the reference blood pressure BP_RF and the reference pulse wave signal PPG_RF (operation S214). The reference blood pressure BP_RF may be displayed through the display unit DSU.

The first blood pressure measurement mode will be described in more detail with reference to FIGS. 6 through 8.

Figure 6:
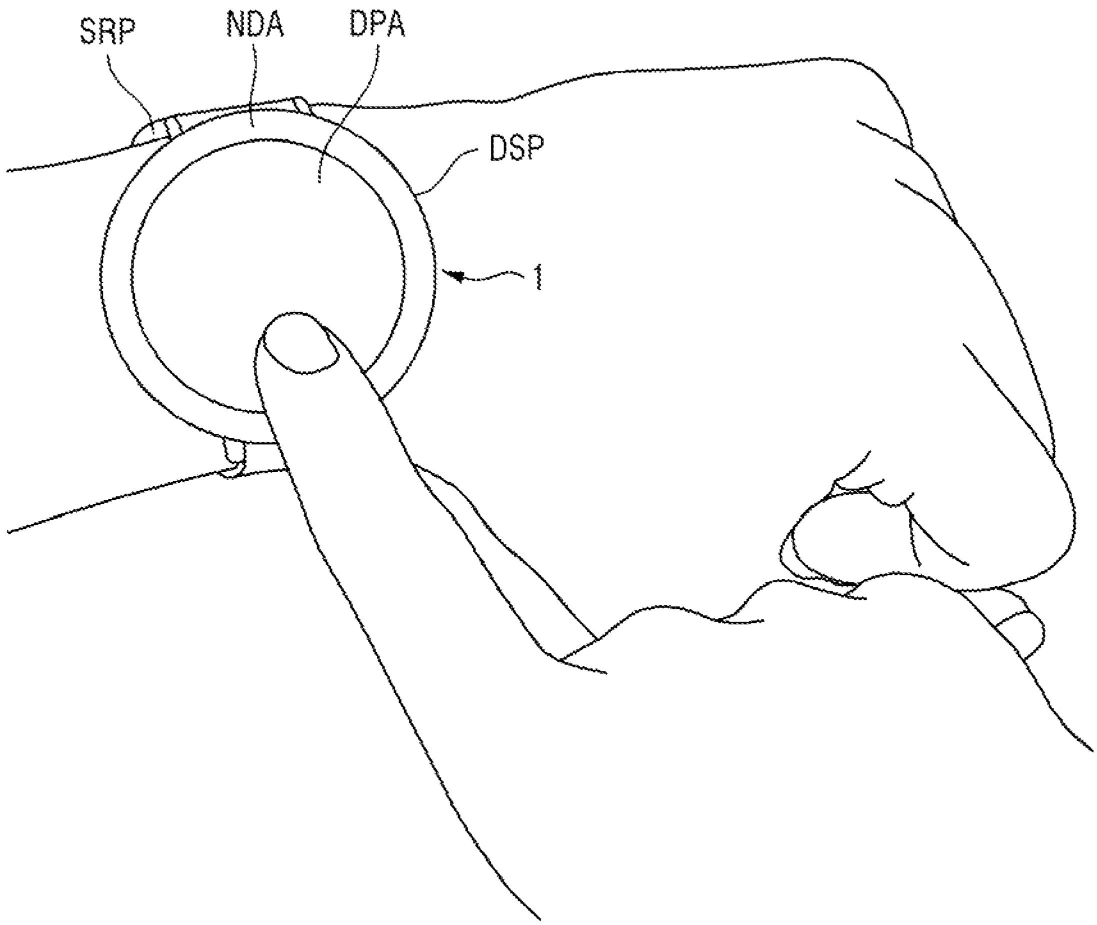
FIG. 6 is a schematic view illustrating a pressure applying operation by a user.
Figure 7:
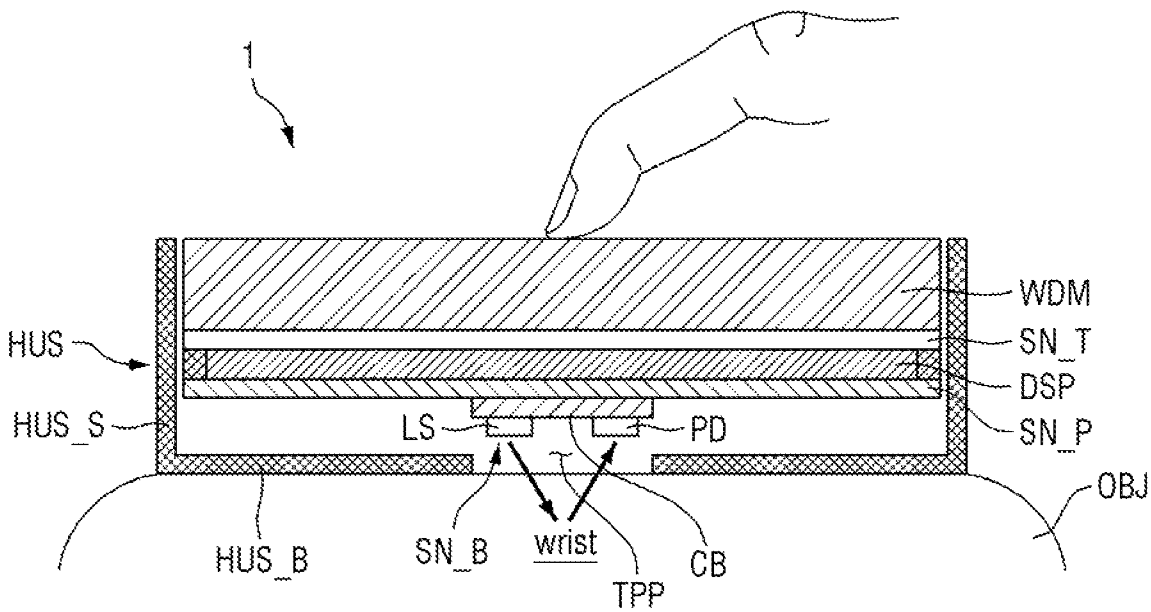
FIG. 7 is a schematic cross-sectional view illustrating the operation of the electronic device in a state where pressure is applied.

FIG. 6 is a schematic view illustrating a pressure applying operation by a user. FIG. 7 is a schematic cross-sectional view illustrating the operation of the electronic device 1 in a state where pressure is applied. FIG. 8 illustrates a pressure graph with respect to time, a pulse wave signal graph with respect to time, and a pulse wave signal graph with respect to pressure in a contact pressure applying operation.

The user may be asked to apply pressure to the electronic device 1 for a predetermined first measurement time. For example, the user may be asked to apply a stronger pressure or a weaker pressure over time during the first measurement time. The user may be asked to apply pressure so that the pressure changes linearly with time. For example, as illustrated in a first graph of FIG. 8, the user may be asked to apply pressure so that the pressure increases linearly with time within the first measurement time. The first measurement time may be, but is not necessarily limited to, in the range of 5 to 80 seconds or in the range of 30 to 40 seconds.

A request to apply pressure to the electronic device 1 may be made to the user through the display unit DSU. For example, the display unit DSU may guide the level of pressure to be applied by the user by showing both a required pressure level and the level of pressure currently input by the user as a chart or numerical values.

The user may apply pressure in various ways in which the pressure sensor SN_P of the electronic device 1 can recognize the applied pressure. For example, as illustrated in FIG. 6, in a state where the electronic device 1 is worn on the wrist, the user may apply pressure to the front of the electronic device 1, for example an upper surface of the electronic device 1 by using a finger, other body part, or other external device. In addition, the user may apply pressure by tightening the strap SRP attached to the electronic device 1. The pressure applying method is not necessarily limited to the above examples. The magnitude of the pressure applied to the upper surface of the electronic device 1 may be measured by the pressure sensor SN_P inside the electronic device 1.

The pressure applied from the upper surface of the electronic device 1 may be transmitted to the user's wrist via the electronic device 1. All of the pressure applied to the upper surface of the electronic device 1 may be transmitted to the user's wrist as it is. However, when the electronic device 1 absorbs some pressure, the pressure reduced by the absorbed pressure may be transmitted to the wrist. The correlation between the pressure applied from the upper surface and the pressure transmitted toward a lower surface of the electronic device 1 may be input to the electronic device 1 in advance. The pressure sensor SN_P (or the blood pressure sensor driving unit DRU_SB) of the electronic device 1 may calculate the magnitude of the pressure transmitted to the wrist based on the magnitude of measured pressure and the pressure transmission correlation, generate the pressure signal PRS, and provide the pressure signal PRS to the first calculator BPC_1.

While the user applies pressure to the electronic device 1, the electronic device 1 and the user's wrist may contact each other. During a corresponding measurement period, as illustrated in FIG. 7, the light source LS of the blood pressure sensor SN_B may emit examination light, and the emitted examination light may travel toward the user's wrist through the light transmitting portion TPP of the housing HUS. When the examination light, for example, infrared light, has a wavelength band that passes through the skin tissue, it may enter the subcutaneous tissue.

Blood vessels located in the subcutaneous tissue are filled with blood, and the amount of blood is different between systole and diastole periods. For example, there may be more blood in systole period and relatively little blood in diastole period. The absorbance of the examination light varies according to the amount of blood, for example the volume of blood. For example, the light absorbance of the tissue may have a maximum value in the systole period of the heart and a minimum value in the diastole period of the heart. Of the examination light entering the subcutaneous tissue, at least some of the light that is not absorbed by blood or other tissues may be reflected by tissue such as bone and then may be incident on the photodetector PD of the blood pressure sensor SN_B. The amount of the reflected light detected by the photodetector PD may represent light absorbance at a corresponding time. From the amount of the reflected light received, the blood pressure sensor SN_B may generate a primary pulse wave signal PPG (a second graph of FIG. 8) that represents the relationship between pulse waves over time. The generated primary pulse wave signal PPG may reflect a change in blood pressure BP according to a heartbeat. The primary pulse wave signal PPG may be stored in the memory MMR as the reference pulse wave signal PPG_RF.

The primary pulse wave signal PPG may include both an alternating current (AC) component and a direct current (DC) component. The blood pressure sensor SN_B (or the blood pressure sensor driving unit DRU_SB) may generate a secondary pulse wave signal PPG (a third graph of FIG. 8) by removing the DC component from the primary pulse wave signal PPG and plotting the primary pulse wave signal PPG without the DC component, according to the magnitude of pressure.

The secondary pulse wave signal PPG represents a pulse wave AC component according to pressure. The blood pressure sensor driving unit DRU_SB may calculate average blood pressure, the highest blood pressure (or systolic blood pressure), and the lowest blood pressure (or diastolic blood pressure) through the secondary pulse wave signal PPG.

For example, the pressure at a point (for example, a point of maximum amplitude) at which a difference between an upper envelope connecting upper ends of oscillating pulse wave AC components and a lower envelope connecting lower ends of the oscillating pulse wave AC components is maximum is calculated as the average blood pressure. Then, the highest blood pressure (systolic blood pressure) and the lowest blood pressure (diastolic blood pressure) may be calculated using the statistically established ratio (e.g., 0.55) of the amplitude of the systolic blood pressure to the amplitude of the average blood pressure and the ratio (e.g., 0.85) of the amplitude of the diastolic blood pressure to the amplitude of the average blood pressure.

Although the method of calculating the blood pressure BP through a standard fixed-ratio algorithm has been described above, the blood pressure calculation algorithm is not necessarily limited thereto. For example, various algorithms known in the art, such as a fixed-slope algorithm and a patient-specific algorithm, can be applied. The above algorithms are described, for example, in U.S. patent Ser. No. 10/398,324, the disclosure of which is incorporated herein in its entirety by reference.

The blood pressure BP calculated through the secondary pulse wave signal PPG may be provided to the memory MMR together with the primary pulse wave signal PPG and may be stored as the reference blood pressure BP_RF and the reference pulse wave signal PPG_RF, respectively.

The second blood pressure measurement mode will now be described. Referring to FIG. 5, when the second blood pressure measurement mode is selected (operation S221), a contact operation is performed. For example a part of the user's body may contact the electronic device 1. In the current operation, contact may be made without application of pressure. For example, the contact operation may be completed when the user wears the electronic device 1 on the wrist, for example, when the electronic device 1 and the wrist, which is a part of the body, come into contact with each other. In the current operation, contact does not mean only complete physical contact. Even if a part of the user's body is physically separated from the electronic device 1, when they are placed close enough for the blood pressure sensor SN_B to receive examination light reflected from the subcutaneous tissue, this may correspond to contact in the current operation. Pressure application may also be performed in the current operation, but the magnitude of pressure according to the pressure application might not be measured, or even if it is measured, it is not utilized to measure the blood pressure BP.

Contact may be made for a predetermined second measurement time. The second measurement time may be the same as or different from the first measurement time. For example, the second measurement time may be less than or equal to the first measurement time. In an embodiment of the present disclosure, the first measurement time may be 40 seconds, and the second measurement time may be 40 seconds or less.

During the second measurement time, the blood pressure sensor SN_B may emit examination light, receive light reflected from the subcutaneous tissue, and generate the pulse wave signal PPG using the reflected light (operation S222). The generated pulse wave signal PPG may be provided to the second calculator BPC_2 of the blood pressure sensor driving unit DRU_SB as the monitoring pulse wave signal PPG_MN. The reference pulse wave signal PPG_RF stored in the memory MMR may also be provided to the second calculator BPC_2. The second calculator BPC_2 may compare and process the monitoring pulse wave signal PPG_MN and the reference pulse wave signal PPG_RF (operation S223) and estimate and calculate the current monitoring blood pressure BP_MN (operation S224).

Figure 9:
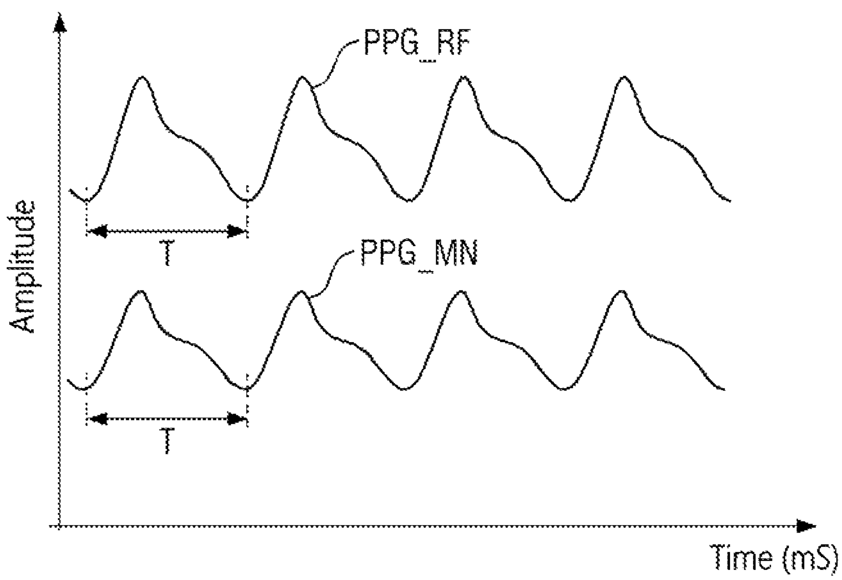
FIG. 9 is a graph illustrating both a reference pulse wave signal and a monitoring pulse wave signal with respect to time.

FIG. 9 is a graph illustrating both the reference pulse wave signal PPG_RF and the monitoring pulse wave signal PPG_MN with respect to time.

Figure 8:
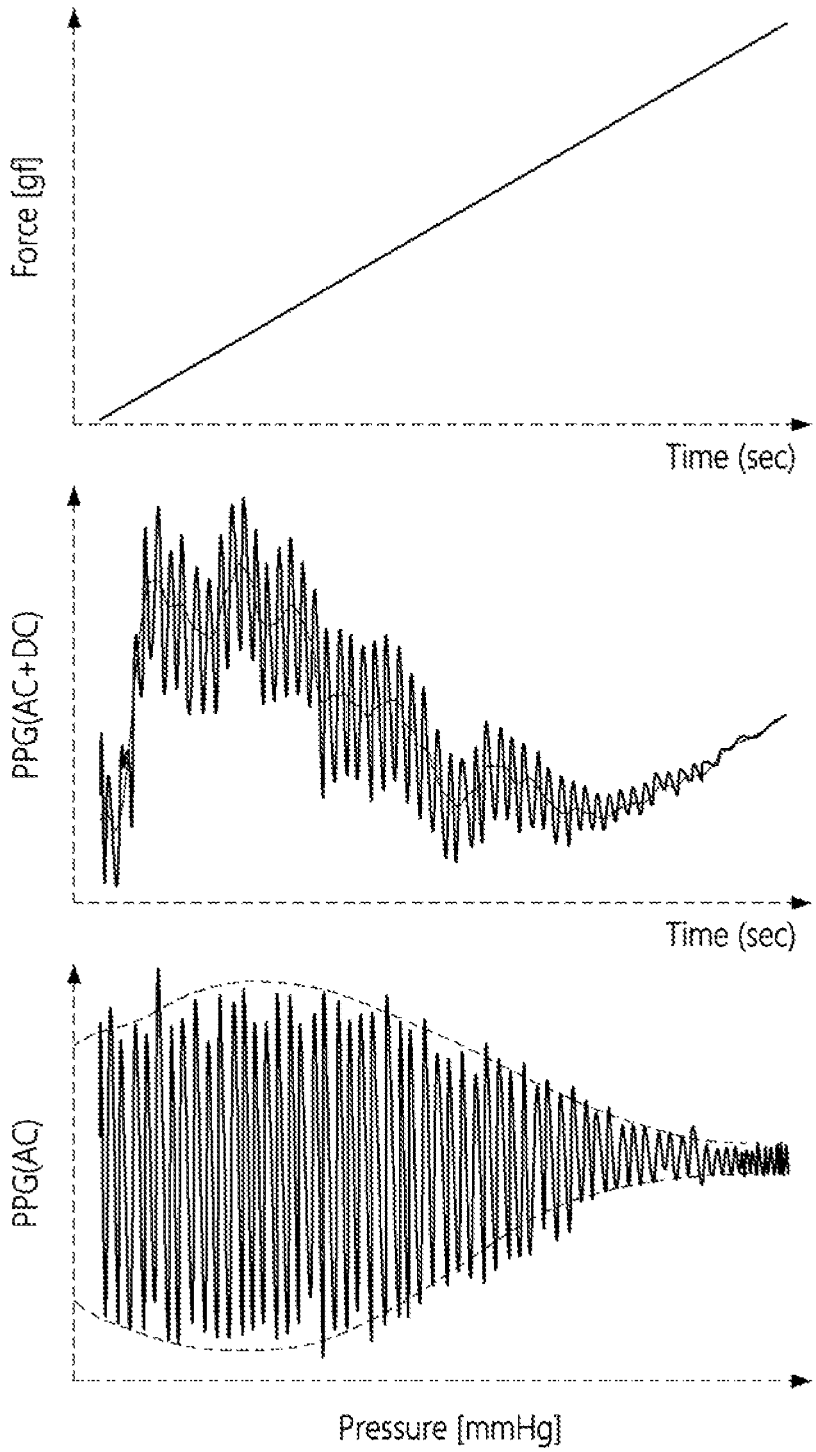
FIG. 8 is a pressure graph with respect to time, a pulse wave signal graph with respect to time, and a pulse wave signal graph with respect to pressure in a contact pressure applying operation.

In FIG. 9, a graph of the reference pulse wave signal PPG_RF is a graph obtained by sampling some sections of the second graph of FIG. 8. In this graph, an amplitude period is illustrated as enlarged by reducing the time scale corresponding to the X-axis. In addition, the monitoring pulse wave signal PPG_MN is illustrated on the same time scale as the reference pulse wave signal PPG_RF.

As illustrated in FIG. 9, since the reference pulse wave signal PPG_RF is a pulse wave signal measured in a state where pressure is applied, it may have a different function value (i.e., y value) from the monitoring pulse wave signal PPG_MN measured in a state where no pressure is applied.

Referring to signal waveforms in units of a period T, a signal waveform of the same shape may be repeated in each of the reference pulse wave signal PPG_RF and the monitoring pulse wave signal PPG_MN. In addition, the reference pulse wave signal PPG_RF and the monitoring pulse wave signal PPG_MN per unit period T may have signal waveforms of substantially similar shapes. The monitoring blood pressure BP_MN, according to the monitoring pulse wave signal PPG_MN, may be calculated by comparing these signal waveforms and applying a correlation according to a difference between the signal waveforms.

Figure 10:
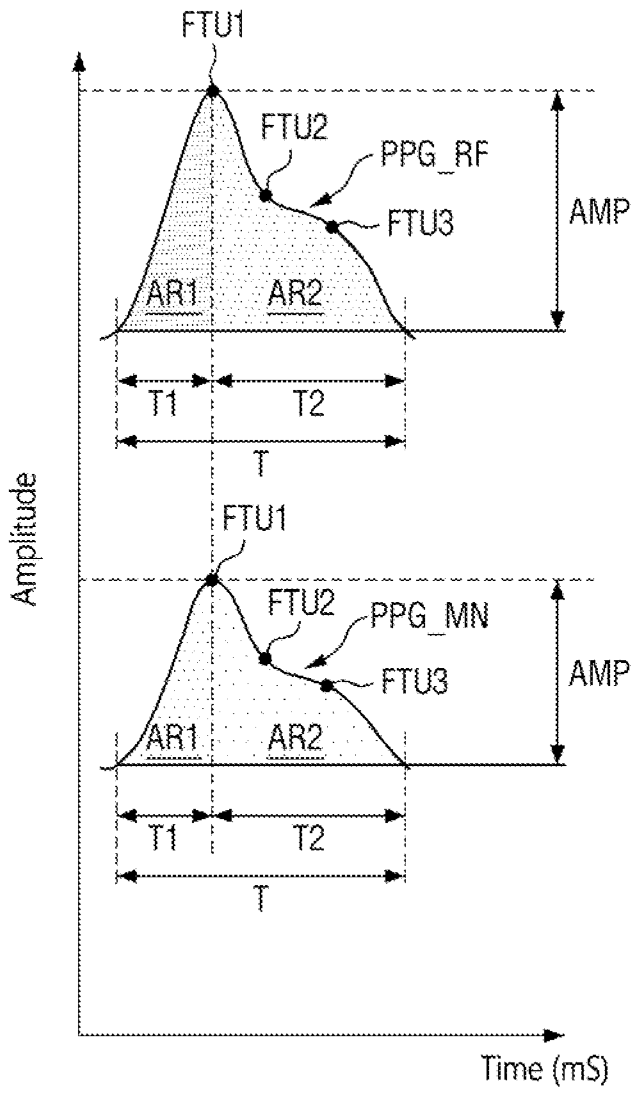
FIG. 10 is a graph comparing the reference pulse wave signal and the monitoring pulse wave signal of one period.

FIG. 10 is a graph comparing the reference pulse wave signal PPG_RF and the monitoring pulse wave signal PPG_MN of one period T.

As illustrated in FIG. 10, the reference pulse wave signal PPG_RF and the monitoring pulse wave signal PPG_MN may each have a period T, an amplitude AMP, an area AR and feature points FTU and may be compared with each other in these aspects.

One period T may be defined as, for example, the time from a lowest point to a next lowest point. One period T may include a first section T1 (or a rising section) from a lowest point to a highest point and a second section T2 (or a falling section) from the highest point to a lowest point again.

The amplitude AMP may be calculated as a difference between the lowest point and the highest point of a waveform.

The area AR may be calculated as an area between the waveform and a line connecting the lowest points. The area AR of one period T may include a first area AR1 of the first section T1 and a second area AR2 of the second section T2.

The feature points FTU may be defined by inflection points of the waveform formed within one period T. For example, the feature points FTU may include, but are not necessarily limited to including, a first feature point FTU1 which is convex upward and located at the highest point at a boundary between the first section T1 and the second section T2, a second feature point FTU2 which is convex downward and located between the highest point and the lowest point, and a third feature point FTU3 which is convex upward and located between the second feature point FTU2 and the lowest point in the second section T2.

The period T, the length of the first period T1, the length of the second period T2, the magnitude of the amplitude AMP, the first area AR1, the second area AR2, and coordinates (e.g., relative coordinates within the period T and the amplitude AMP) of the first through third feature points FTU1 through FTU3 may be calculated for each of the reference pulse wave signal PPG_RF and the monitoring pulse wave signal PPG_MN and may be compared between the reference pulse wave signal PPG_RF and the monitoring pulse wave signal PPG_MN.

Figure 11:
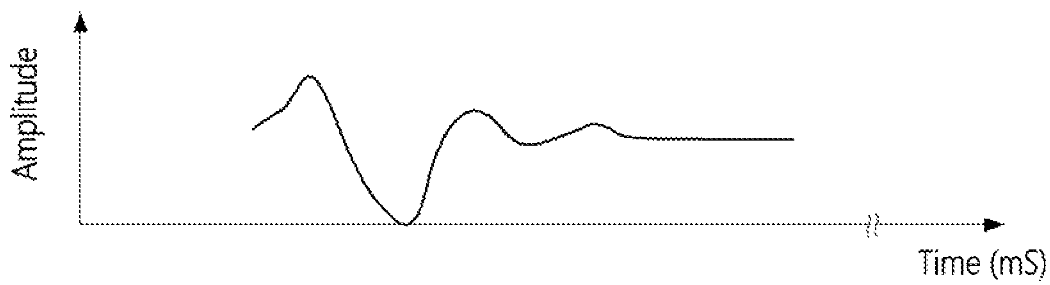
FIG. 11 is a quadratic differential function graph of the monitoring pulse wave signal.

FIG. 11 is a quadratic differential function graph of the monitoring pulse wave signal PPG_MN.

As illustrated in FIG. 11, a graph having a plurality of inflection points may be obtained through quadratic differentiation of the monitoring pulse wave signal PPG_MN. Similarly, a graph having a plurality of inflection points may be obtained through quadratic differentiation of the reference pulse wave signal PPG_RF. After the quadratic differential function graphs are obtained for the reference pulse wave signal PPG_RF and the monitoring pulse wave signal PPG_MN, respectively, coordinates of the inflection points may be compared with each other.

The memory MMR of the blood pressure sensor driving unit DRU_SB may have data (e.g., a lookup table) about the blood pressure BP determined according to the above-described waveform differences (period, amplitude, area, feature points, quadratic differential function graph, etc.) between the reference pulse wave signal PPG_RF and the monitoring pulse wave signal PPG_MN. The second calculator BPC_2 may calculate the monitoring blood pressure BP_MN (average blood pressure, systolic blood pressure, diastolic blood pressure, etc.) in the second blood pressure measurement mode by calculating the above-described waveform differences between the reference pulse wave signal PPG_RF and the monitoring pulse wave signal PPG_MN and applying a correlation stored in the memory MMR to the values of the waveform differences.

Unlike in the first blood pressure measurement mode, in the second blood pressure measurement mode described above, the blood pressure BP can be measured even if a user does not apply pressure required during a measurement time. Therefore, simple blood pressure measurement is possible. In addition, since the blood pressure BP can be measured simply when the user wears the electronic device 1 to be in contact with a part of the user's body, the blood pressure BP can be monitored in real time.

Although the second blood pressure measurement mode does not use the pressure signal PRS, it uses the pressure sensor SN_P. Therefore, the reference pulse wave signal PPG_RF with relatively high accuracy is utilized. Accordingly, the blood pressure BP can be measured more accurately.

In the current embodiment, the monitoring pulse wave signal PPG_MN and the reference pulse wave signal PPG_RF compared with each other may be obtained in substantially the same manner, which may also help to increase the accuracy of blood pressure measurement. For example, when a cuff is used to determine the reference blood pressure BP_RF, a signal calculated to measure the monitoring blood pressure BP_MN and a signal obtained to determine the reference blood pressure BP_RF may have completely different types of signal waveforms. In order to determine the blood pressure BP by comparing the signals calculated in such completely different manners, a process of converting different signal waveforms is required, and in this process, the possibility of an increase in measurement error may increase. As in the embodiment, when the blood pressure BP is determined by comparing the monitoring pulse wave signal PPG_MN and the reference pulse wave signal PPG_RF obtained in substantially the same manner for the same body part (e.g., the wrist) of the same person, the possibility of occurrence of errors due to signal waveform conversion can be reduced.

In some embodiments, the electronic device 1 may further include an electrocardiogram sensor. When the electronic device 1 includes the electrocardiogram sensor, the electrocardiogram sensor may measure a user's electrocardiogram during the first measurement time and/or the second measurement time and generate an electrocardiogram signal. When the electrocardiogram signal and the pulse wave signal PPG (e.g., the reference pulse wave signal PPG_RF and/or the monitoring pulse wave signal PPG_MN) are compared on the same time axis, the time between a peak of the electrocardiogram signal and a peak of the pulse wave signal PPG can be calculated as a pulse transit time. A pulse wave velocity may be calculated by dividing the distance from the heart to the peripheral blood vessels (i.e., to the user's wrist) by the pulse transit time. Since the pulse wave velocity is related to the difference between systolic blood pressure and diastolic blood pressure, the user's blood pressure BP can be estimated using the pulse wave velocity. Similar concepts are described in detail in, for example, Korean Patent Publication No. 10-2021-0091559, the disclosure of which is incorporated herein in its entirety by reference.

In the present specification, the blood pressure BP estimated using the pulse wave velocity calculated from the electrocardiogram signal may be referred to as auxiliary blood pressure. The auxiliary blood pressure may be used to increase the accuracy of the blood pressure BP measured in the first blood pressure measurement mode or the second blood pressure measurement mode described above.

For example, the blood pressure BP_RF measured in the first blood pressure measurement mode may be compared with first auxiliary blood pressure measured during the same measurement time (the first measurement time), and a difference value between them may be stored as reference data in the memory MMR.

In addition, the blood pressure BP_MN measured in the second blood pressure measurement mode may be compared with second auxiliary blood pressure measured during the same measurement time (e.g., the second measurement time). The electronic device 1 may verify the accuracy of the blood pressure BP_MN measured in the second blood pressure measurement mode by comparing the blood pressure BP_MN measured in the second blood pressure measurement mode with the second auxiliary blood pressure. When a difference between the blood pressure BP_MN measured in the second blood pressure measurement mode and the second auxiliary blood pressure is large, the determined blood pressure BP may be corrected based on the second auxiliary blood pressure and the difference value stored in the reference data, or the blood pressure BP may be re-measured.

Figure 12:
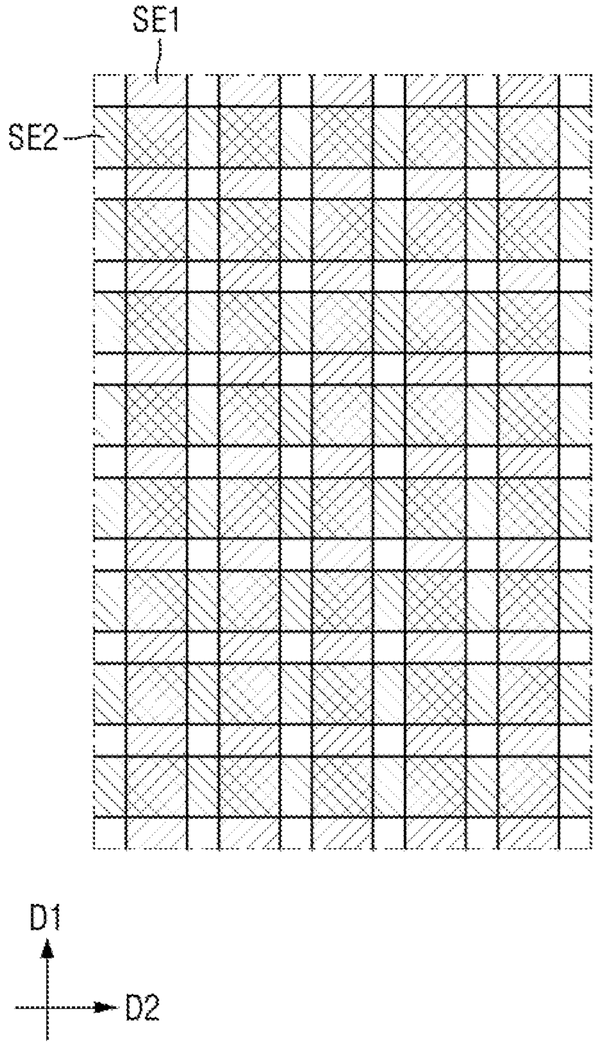
FIG. 12 is a schematic layout view of a pressure sensor according to an embodiment of the present disclosure.
Figure 13:
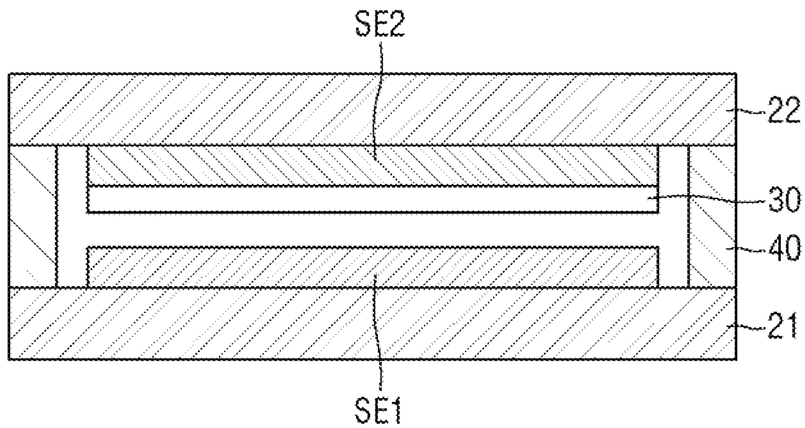
FIG. 13 is a cross-sectional view of the pressure sensor of FIG. 12.

Structures of the pressure sensor SN_P according to various embodiments applicable to the electronic device 1 will now be described. 100150I FIG. 12 is a schematic layout view of a pressure sensor SN_P according to an embodiment of the present disclosure. FIG. 13 is a cross-sectional view of the pressure sensor SN_P of FIG. 12. FIGS. 12 and 13 illustrate the structure of a force sensor as an example of the pressure sensor SN_P.

Referring to FIGS. 12 and 13, the pressure sensor SN_P may include first electrodes SE1, second electrodes SE2, and a pressure sensing layer 30 disposed between the first electrodes SE1 and the second electrodes SE2.

Each of the first and second electrodes SE1 and SE2 may include a conductive material. For example, each of the first and second electrodes SE1 and SE2 may include a metal such as silver (Ag) or copper (Cu), a transparent conductive oxide such as ITO, IZO or ZIO, carbon nanotubes, or a conductive polymer. Any one of the first and second electrodes SE1 and SE2 may be a driving electrode, and the other may be a sensing electrode.

The pressure sensing layer 30 may include a pressure sensitive material. The pressure sensitive material may include carbon or metal nanoparticles such as nickel, aluminum, tin or copper. The pressure sensitive material may be disposed within a polymer resin in the form of particles, but the present disclosure is not necessarily limited thereto. In the pressure sensing layer 30, the electrical resistance of the pressure sensitive material decreases as the pressure increases. Therefore, it is possible to sense whether pressure has been applied and the magnitude of the pressure by measuring the electrical resistance of the pressure sensing layer 30 through the first electrodes SE1 and the second electrodes SE2. The pressure sensing layer 30 may either be transparent or opaque.

In some embodiments, the first electrodes SE1 and the second electrodes SE2 may be arranged in a line type. For example, a plurality of first electrodes SE1 may extend parallel to each other in a first direction D1, and a plurality of second electrodes SE2 may extend in a direction intersecting the first direction D1, for example, in a second direction D2 perpendicular to the first direction DR1. The first electrodes SE1 and the second electrodes SE2 have a plurality of overlap areas at their intersections. The overlap areas may be arranged in a matrix. Each overlap area may be a pressure sensing cell. For example, the pressure sensing layer 30 may be disposed in each overlap area to sense pressure at a corresponding position.

In an embodiment of the present disclosure, the pressure sensor SN_P may include two sensor substrates facing each other. Each sensor substrate may include a substrate 21 or 22. A first substrate 21 of a first sensor substrate and a second substrate 22 of a second sensor substrate may each include a polyethylene, polyimide, polycarbonate, polysulfone, polyacrylate, polystyrene, polyvinyl chloride, polyvinyl alcohol, polynorbonene, polyester-based material. In an embodiment of the present disclosure, the first substrate 21 and the second substrate 22 may be made of a polyethylene terephthalate (PET) film or a polyimide film.

The first electrodes SE1, the second electrodes SE2, and the pressure sensing layer 30 may be included in the first sensor substrate or the second sensor substrate. For example, the first electrodes SE1 and the pressure sensing layer 30 may be included in the first sensor substrate, and the second electrodes SE2 may be included in the second sensor substrate. The first electrodes SE1 may be disposed on a surface of the first substrate 21 which faces the second substrate 22. The second electrodes SE2 may be disposed on a surface of the second substrate 22 which faces the first substrate 21, and the pressure sensing layer 30 may be disposed on the second electrodes SE2. The first sensor substrate and the second sensor substrate may be bonded together by a bonding layer 40. The bonding layer 40 may be disposed along edges of each sensor substrate, but the present disclosure is not necessarily limited thereto.

In an embodiment of the present disclosure, the first electrodes SE1, the second electrodes SE2, and the pressure sensing layer 30 may be included in one sensor substrate. For example, the first electrodes SE1 may be disposed on a surface of the first substrate 21, the pressure sensing layer 30 may be disposed on the first electrodes SE1, and the second electrodes SE2 may be disposed on the pressure sensing layer 30.

The pressure sensor SN_P including the above-described force sensor may be either transparent or opaque. In the case of a transparent pressure sensor SN_P, the first substrate 21 and the second substrate 22 may be made of a transparent material, the first electrodes SE1 and the second electrodes SE2 may be made of a transparent conductive material, and the pressure sensing layer 30 may also be made of a transparent material. In the case of an opaque pressure sensor SN_P, an electrode or a pressure-sensitive material may be selected from various materials regardless of whether the materials are transparent or not.

Figure 14:
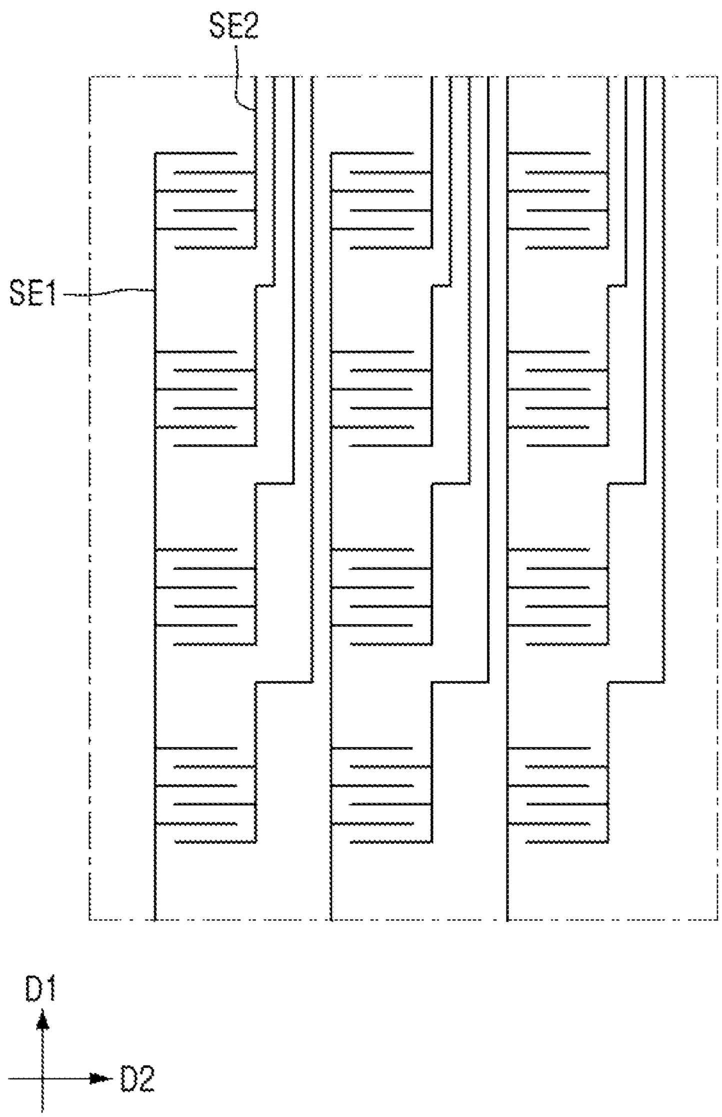
FIG. 14 is a schematic layout view of a pressure sensor according to an embodiment of the present disclosure.
Figure 15:
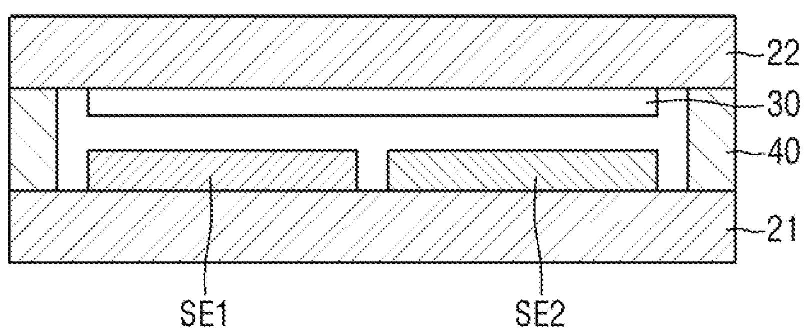
FIG. 15 is a cross-sectional view of the pressure sensor of FIG. 14.

FIG. 14 is a schematic layout view of a pressure sensor SN_P according to an embodiment of the present disclosure. FIG. 15 is a cross-sectional view of the pressure sensor SN_P of FIG. 14. FIGS. 14 and 15 illustrate another structure of the force sensor.

Referring to FIGS. 14 and 15, the pressure sensor SN_P, according to the current embodiment, is different from the embodiment of FIGS. 12 and 13 in that first electrodes SE1 and second electrodes SE2 are disposed on the same layer. For example, the first electrodes SE1 and the second electrodes SE2 are disposed on a surface of a first substrate 21. The first electrodes SE1 and the second electrodes SE2 are disposed adjacent to each other. The first and second electrodes SE1 and SE2 may each include a plurality of branch portions and may be in the shape of a comb electrode in which the branch portions are alternately disposed. A pressure sensing layer 30 is formed on a second substrate 22 and disposed above the first electrodes SE1 and the second electrodes SE2.

In the current embodiment, the first electrodes SE1 and the second electrodes SE2 do not overlap each other in the thickness direction, but are disposed adjacent to each other in plan view. When pressure is applied, an electric current may flow between the first and second electrodes SE1 and SE2 through the pressure sensing layer 30 above them. This structure may be used for measuring shear force.

Figure 16:
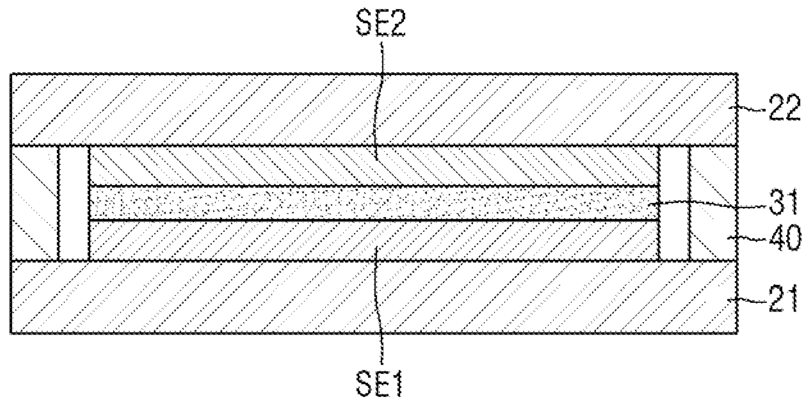
FIG. 16 is a cross-sectional view of a pressure sensor according to an embodiment of the present disclosure.

FIG. 16 is a cross-sectional view of a pressure sensor SN_P according to an embodiment of the present disclosure. FIG. 16 illustrates a gap capacitor as an example of the pressure sensor SN_P.

Referring to FIG. 16, the pressure sensor SN_P, according to the current embodiment, may include a first electrode SE1, a second electrode SE2, and a variable dielectric constant material layer 31 disposed between the first electrode SE1 and the second electrode SE2. The pressure sensor SN_P, according to the current embodiment, may have substantially the same structure as the pressure sensor SNP according to the embodiment of FIGS. 12 and 13 except that the variable dielectric constant material layer 31 is disposed between the first electrode SE1 and the second electrode SE2 instead of the pressure sensing layer 30.

The variable dielectric constant material layer 31 is a material whose dielectric constant varies according to applied pressure, and various materials known in the art may be applied as the variable dielectric constant material layer 31. Since the dielectric constant of the variable dielectric constant material layer 31 varies according to applied pressure, the magnitude of the applied pressure may be measured by measuring a capacitance value between the first electrode SE1 and the second electrode SE2.

The pressure sensor SN_P including the above-described gap capacitor may be either transparent or opaque. In the case of a transparent pressure sensor SN_P, the first electrode SE1 and the second electrode SE2 may be made of a transparent conductive material, and the variable dielectric constant material layer 31 may also be made of a transparent material. In the case of an opaque pressure sensor SN_P, an electrode or a pressure-sensitive material may be selected from various materials regardless of whether the materials are transparent or not.

Figure 17:
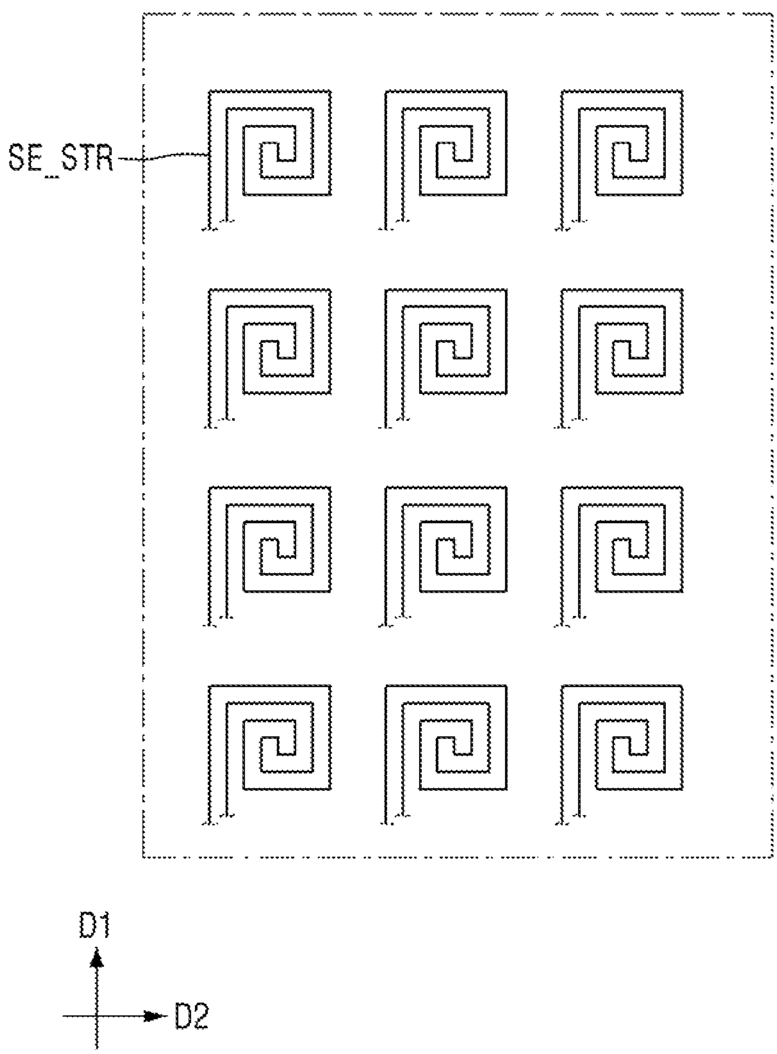
FIG. 17 is a layout view of a pressure sensor according to an embodiment of the present disclosure.

FIG. 17 is a layout view of a pressure sensor SN_P according to an embodiment of the present disclosure. FIG. 17 illustrates a strain gauge as an example of the pressure sensor SN_P.

Referring to FIG. 17, the pressure sensor SN_P may include strain sensing electrodes SE_STR. The strain sensing electrodes SE_STR may be patterns of a conductive layer formed on a first substrate 21 (see FIG. 13). An insulating layer or a second substrate 22 (see FIG. 13) may be disposed on the strain sensing electrodes SE_STR, but the present disclosure is not necessarily limited thereto.

The shape of the strain sensing electrodes SE_STR changes as pressure is applied thereto. When the shape of the strain sensing electrodes SE_SIR changes, the resistance value of the strain sensing electrodes SE_STR also changes. Therefore, the magnitude of the pressure may be measured by measuring the resistance value of the strain sensing electrodes SE_STR.

In order to maximize a change in resistance value according to pressure, each of the strain sensing electrodes SE_STR may have a serpentine shape including a plurality of bent portions in plan view. For example, as illustrated in FIG. 17, each of the strain sensing electrodes SE_STR may have a tornado shape that repeats extending to one side in the first direction D1, being bent, extending to the other side in the second direction D2, being bent again, extending to the other side in the first direction DR1, being bent again, and extending to one side in the second direction D2. As an example, each of the strain sensing electrodes SE_STR may have a zigzag shape. However, it will be understood that the planar shape of the strain sensing electrodes SE_STR is not necessarily limited to the illustrated example, and more various modifications are possible.

The pressure sensor SN_P including the above-described strain gauge may be either transparent or opaque. In the case of a transparent pressure sensor SN_P, the strain sensing electrodes SE_STR may be made of a transparent conductive material. In the case of an opaque pressure sensor SN_P, the strain sensing electrodes SE_STR may be selected from various materials regardless of whether the materials are transparent or not.

Hereinafter, more various embodiments of the electronic device 1 will be described. In the following embodiments, a description of elements already described will be omitted or given briefly, and differences will be mainly described.

Figure 18:
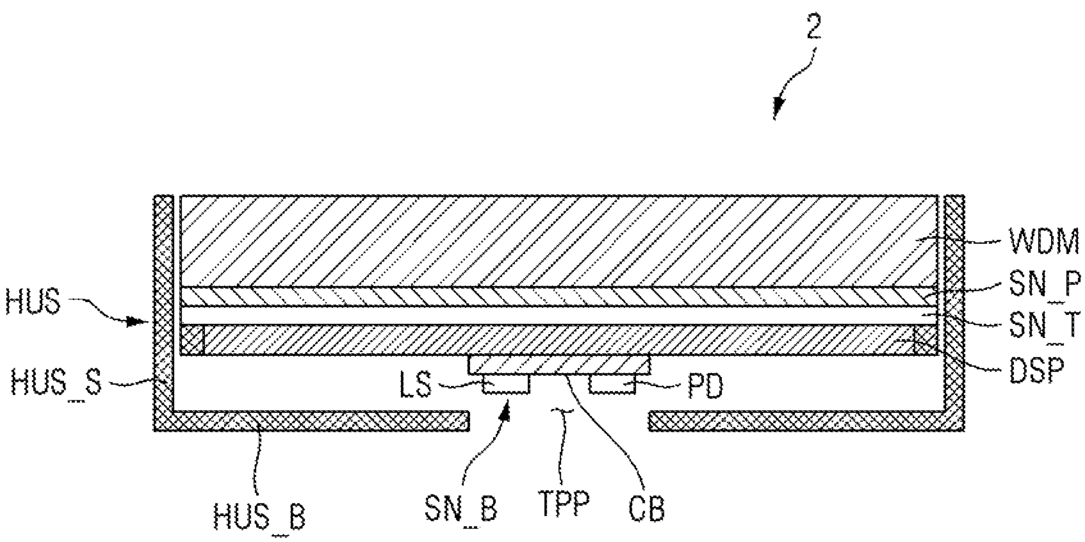
FIGS. 18 and 19 are cross-sectional views of electronic devices according to embodiments of the present disclosure.
Figure 19:
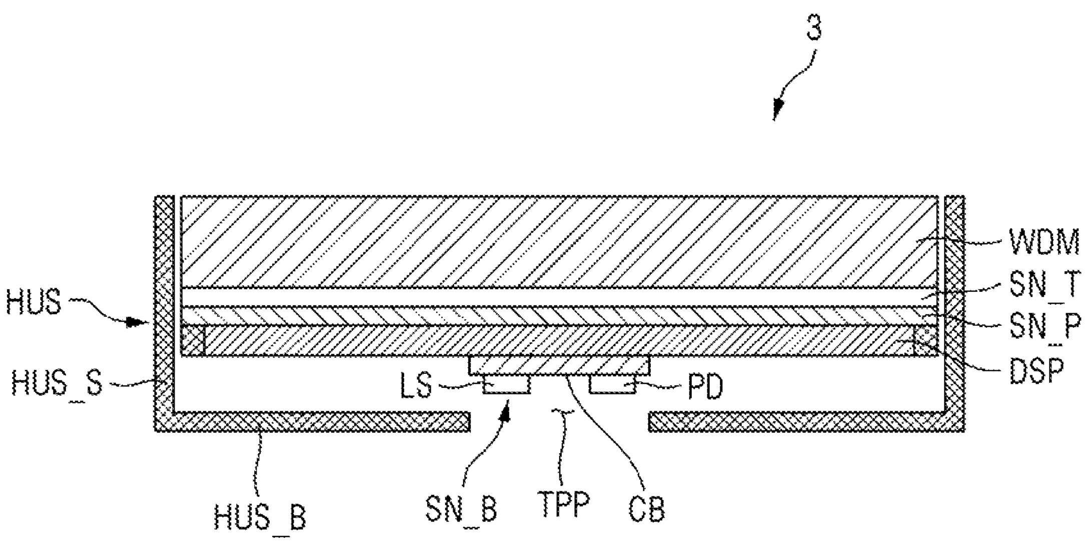

FIGS. 18 and 19 are cross-sectional views of electronic devices 2 and 3 according to embodiments of the present disclosure. The electronic devices 2 and 3, according to the embodiments of FIGS. 18 and 19, are different from that according to the embodiment of FIG. 3 in the position of a pressure sensor SN_P.

For example, the pressure sensor SN_P may be disposed on a display panel DSP. In this case, the pressure sensor SN_P may be transparent so as not to obstruct the display of the display panel DSP. As an example, the pressure sensor SN_P may be disposed in a non-display area NDA other than a display area DPA of the display panel DSP. When the pressure sensor SN_P is disposed in the non-display area NDA of the display panel DSP, even if the pressure sensor SN_P itself does not have high light transmittance, it might not obstruct the display of the display panel DSP.

The pressure sensor SN_P may be disposed on a touch sensor SN_T as illustrated in FIG. 18. Alternatively, the pressure sensor SN_P may be disposed between the display panel DSP and the touch sensor SN_T as illustrated in FIG. 19.

Figure 20:
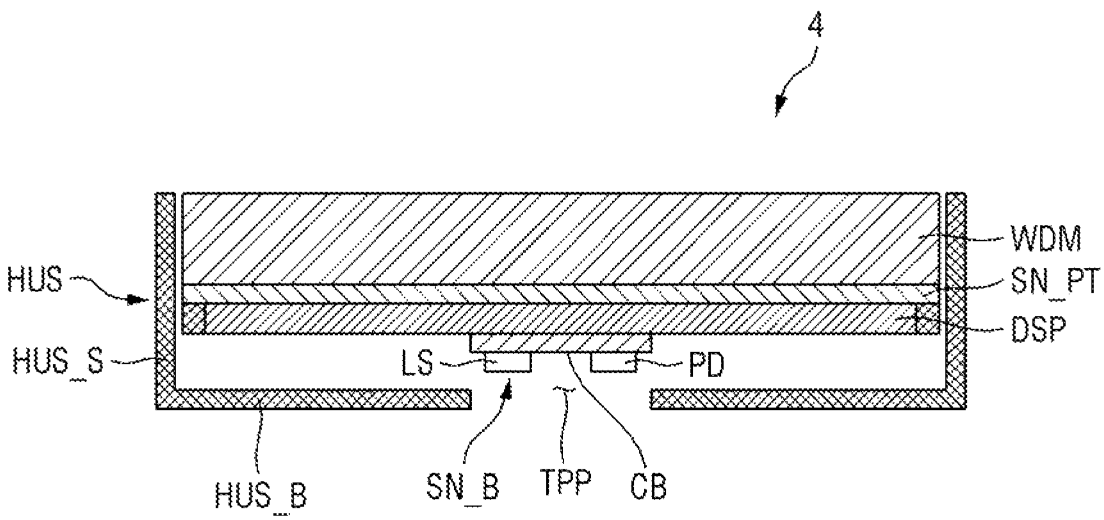
FIG. 20 is a cross-sectional view of an electronic device according to an embodiment of the present disclosure.

FIG. 20 is a cross-sectional view of an electronic device 4 according to an embodiment of the present disclosure.

Referring to FIG. 20, the electronic device 4, according to the current embodiment, shows that a pressure sensor SN_P and a touch sensor SN_T can be integrated. As illustrated in FIG. 20, the electronic device 4 may include a pressure/touch sensor SN_PT including both a pressure sensing function and a touch sensing function. For example, in the pressure/touch sensor SN_PT, a pressure sensing electrode and a touch sensing electrode may be formed on the same layer. In this case, the pressure sensing electrode and the touch sensing electrode might not overlap each other in the thickness direction.

In addition, the pressure sensing electrode and the touch sensing electrode may share a part with each other.

In some embodiments, the pressure sensing electrode and the touch sensing electrode may be formed with an interlayer insulating layer interposed between them.

When the pressure sensor SN_P and the touch sensor SN_T are integrated as described above, a thickness of the electronic device 4 can be reduced, and manufacturing costs can be reduced.

Figure 21:
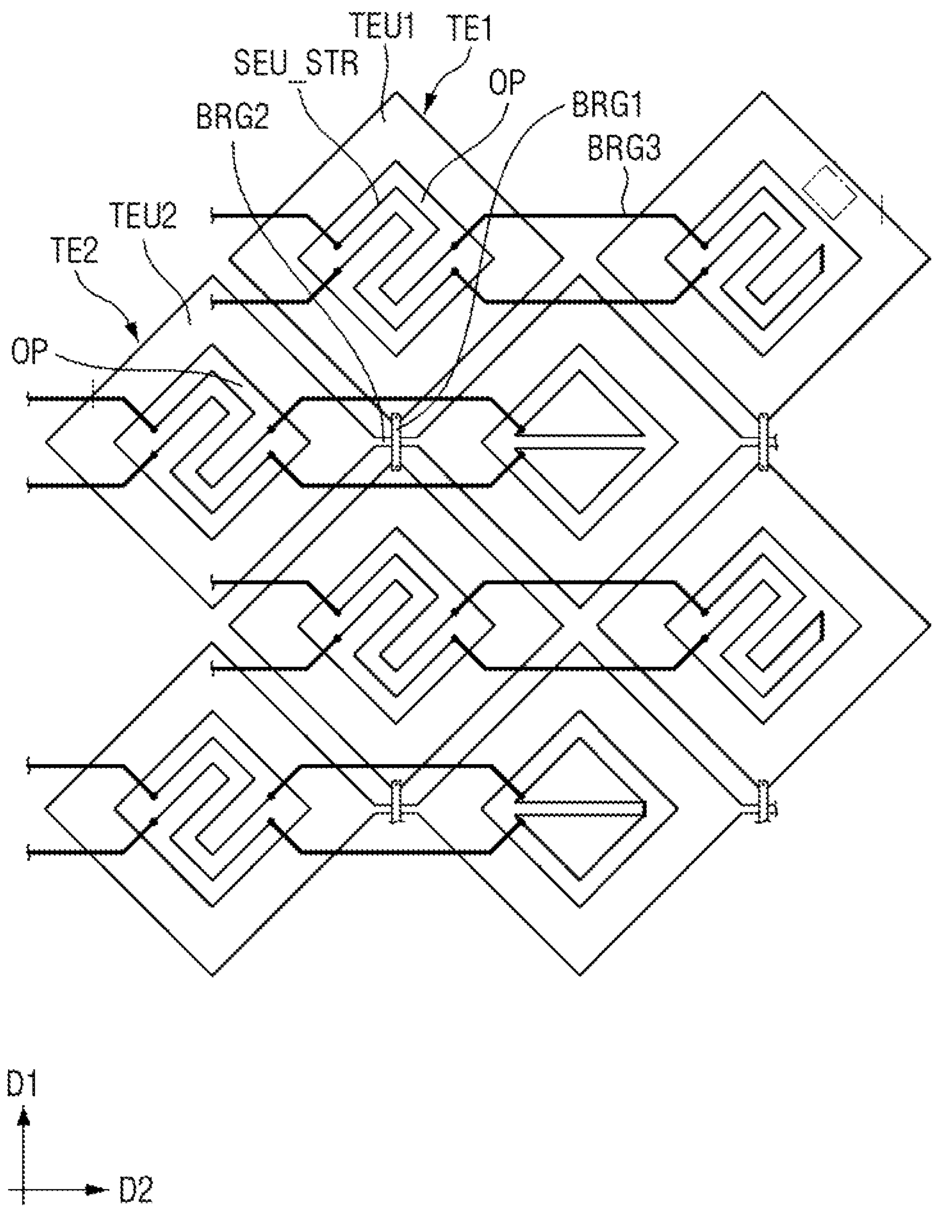
FIG. 21 is an example layout view of a pressure/touch sensor of FIG. 20.

FIG. 21 is an example layout view of the pressure/touch sensor SN_PT of FIG. 20.

Referring to FIG. 21, touch electrodes TE may include a plurality of first touch sensing electrodes TE1 extending in the first direction D1 and a plurality of second touch sensing electrodes TE2 extending in the second direction D2. Each of the first touch sensing electrodes TE1 may include a plurality of first unit electrodes TEU1 having a substantially rhombus shape and arranged along the first direction D1 and a first connection portion BRG1 connecting the first unit electrodes TEU1. Each of the second touch sensing electrodes TE2 may include a plurality of second unit electrodes TEU2 having a substantially rhombus shape and arranged along the second direction D2 and a second connection portion BRG2 connecting the second unit electrodes TEU2. The first unit electrodes TEU1, the second unit electrodes TEU2, and the second connection portion BRG2 may be made of a first conductive layer, and the first connection portion BRG1 may be made of a second conductive layer disposed on the first conductive layer with an insulating layer interposed between them.

Each of the first and second unit electrodes TEU1 and TEU2 may include an internal opening OP. A unit strain gauge electrode SEU_STR may be disposed in the internal opening OP of each of the first and second unit electrodes TEU1 and TEU2. The unit strain gauge electrodes SEU_STR neighboring each other along the second direction D2 may be connected to each other through a strain bridge electrode BRG3. The unit strain gauge electrodes SEU_STR may be connected through the strain bridge electrode BRG3 to form a strain gauge. The unit strain gauge electrodes SEU_STR may be made of the first conductive layer, and the strain bridge electrode BRG3 may be made of the second conductive layer.

Unlike in the above example, a strain gauge may also be formed in an area that is not related to an area in which a touch sensing electrode is disposed.

Figure 22:
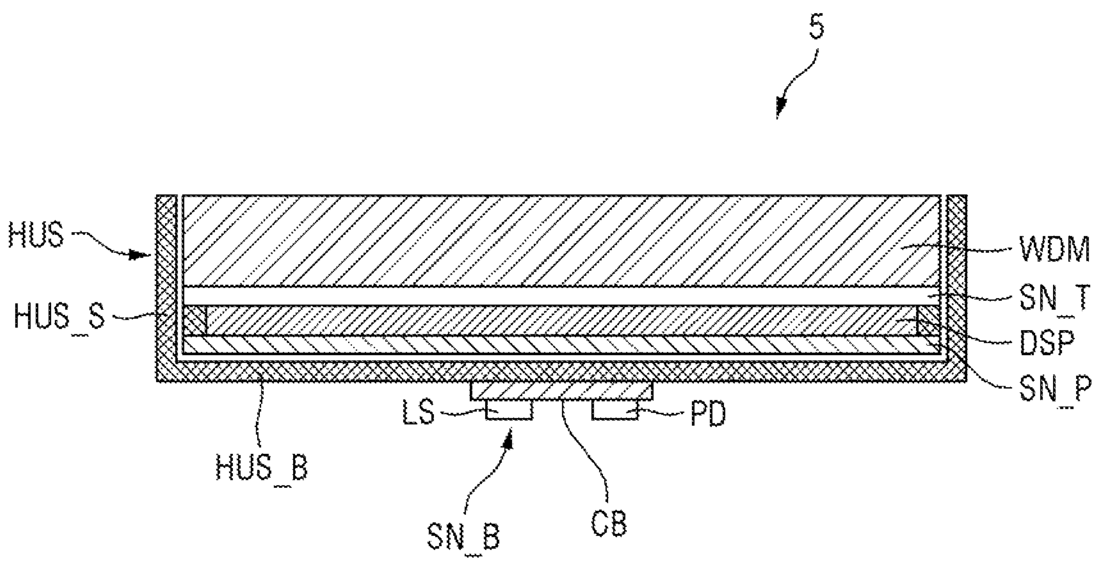
FIG. 22 is a cross-sectional view of an electronic device according to an embodiment of the present disclosure.

FIG. 22 is a cross-sectional view of an electronic device 5 according to an embodiment of the present disclosure.

Referring to FIG. 22, the electronic device 5, according to the current embodiment, is different from that according to the embodiment of FIG. 4 in that a light source LS and a photodetector PD of a blood pressure sensor SN_B are disposed outside a housing HUS. The light source LS and the photodetector PD are mounted on a circuit board CB. The circuit board CB may be attached to a bottom surface of a bottom portion HUS_B of the housing HUS through an adhesive member or the like. In the current embodiment, since the light source LS and the photodetector PD are disposed outside the housing HUS, the bottom portion HUS_B of the housing HUS does not need to include a light transmitting portion TPP such as an opening, unlike in the embodiment of FIG. 4.

Figure 23:
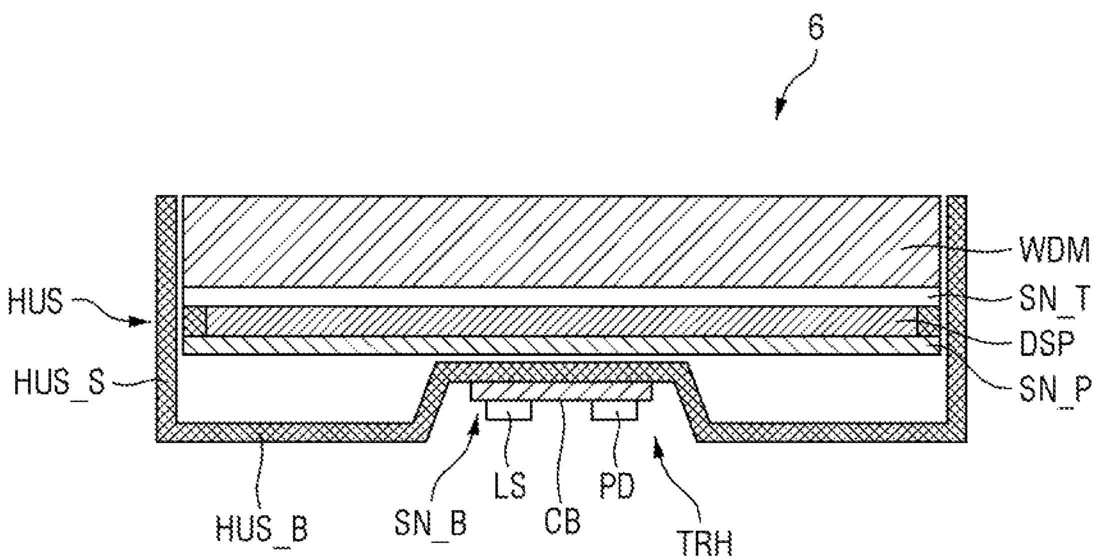
FIG. 23 is a cross-sectional view of an electronic device according to an embodiment of the present disclosure.

FIG. 23 is a cross-sectional view of an electronic device 6 according to an embodiment of the present disclosure.

Referring to FIG. 23, the electronic device 6, according to the current embodiment, is the same as that according to the embodiment of FIG. 22 in that a light source LS and a photodetector PD of a blood pressure sensor SN_B are disposed outside a housing HUS but is different from the embodiment of FIG. 22 in that a bottom portion HUS_B of the housing HUS includes a receiving groove TRH for accommodating the light source LS and the photodetector PD in a bottom surface thereof. A depth of the receiving groove TRH may be greater than or equal to a maximum height of a structure including a blood pressure sensor module, which includes a circuit board CB and the light source LS and the photodetector PD mounted on the circuit board CB, and an adhesive member used for coupling of the blood pressure sensor module. When the receiving groove TRH has the above-described depth, the blood pressure sensor module might not protrude from the bottom surface of the bottom portion HUS_B of the surrounding housing HUS. Therefore, the blood pressure sensor module can be effectively protected, and wearing comfort can be increased.

Figure 24:
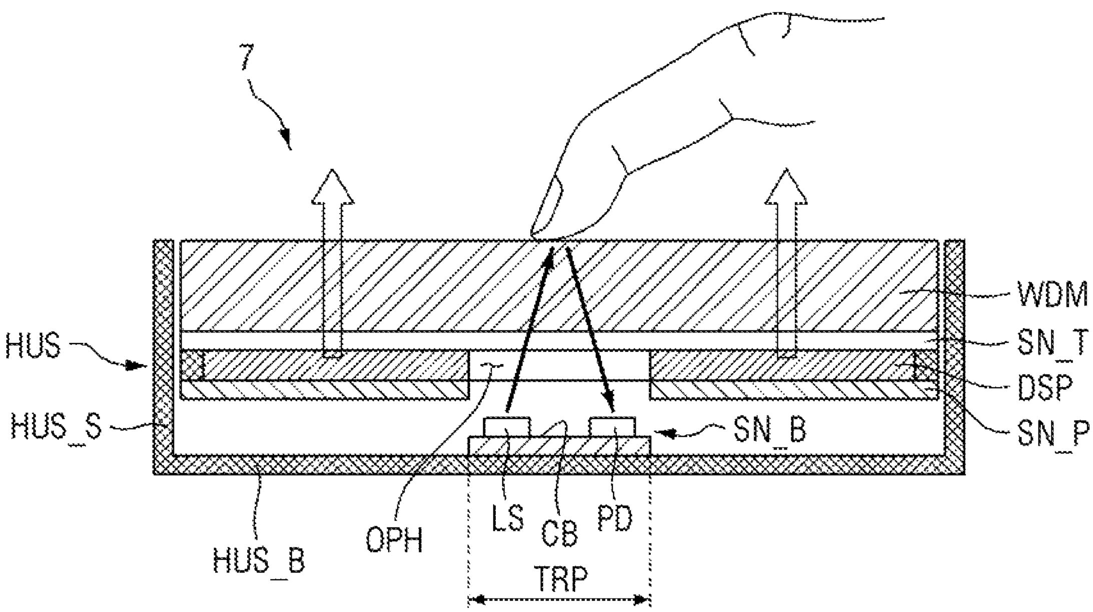
FIG. 24 is a cross-sectional view of an electronic device according to an embodiment of the present disclosure.

FIG. 24 is a cross-sectional view of an electronic device 7 according to an embodiment of the present disclosure.

Referring to FIG. 24, the electronic device 7, according to the current embodiment, is different from that according to the embodiment of FIG. 4 in that a light source LS and a photodetector PD of a blood pressure sensor SN_B are placed to face upwardly. The light source LS and the photodetector PD may be accommodated in a housing HUS in a state where they are mounted on a circuit board CB. Here, the circuit board CB may be disposed under the light source LS and the photodetector PD. The circuit board CB may be attached onto an upper surface of a bottom portion HUS_B of the housing HUS by an adhesive member interposed between them, but the present disclosure is not necessarily limited thereto. In the current embodiment, examination light is emitted upward, and reflected light is also incident and received from above. Therefore, even if a light transmitting portion TPP is not formed in the housing HUS, unlike in the embodiment of FIG. 4, blood pressure BP can be measured without problem.

A user' body part where the blood pressure BP is measured applies pressure and/or makes contact through a protective member WDM as illustrated in the drawing. Examination light emitted from the light source LS reaches the user's body part through a space in which a pressure sensor SN_P, a display panel DSP, a touch sensor SN_T, and the protective member WDM are located above the light source LS. In addition, light reflected from the subcutaneous tissue of the user's body part is incident on the photodetector PD in reverse order. In order to facilitate the entry and exit of the examination light and the reflected light, a light transmitting area TRP may be defined in at least a portion of the electronic device 7. The light transmitting area TRP may be defined, for example, in an area overlapping the light source LS and the photodetector PD.

Among the stacked members, a transparent member in itself does not require a structural change in the light transmitting area TRP, but an opaque or low transmittance member may require a structural modification to increase transmittance in the light transmitting area TRP.

For example, since the protective member WDM and the touch sensor SN_T themselves have high transmittance, they do not need to have a particularly different structure in the light transmitting area TRP. Members having transmittance lower than desired transmittance for blood pressure sensing, such as the display panel DSP and the pressure sensor SN_P, may include an optical hole OPH to increase the transmittance of the members in the light transmitting area TRP. The optical hole OPH may be a physically penetrated opening or may be an area treated to have higher transmittance than other surrounding areas. For example, the display panel DSP may include a substrate, a metal layer, a semiconductor layer, and an insulating layer. Here, at least some of the substrate, the metal layer, the semiconductor layer, and the insulating layer may be selectively removed in the light transmitting area TRP to selectively increase the transmittance of the display panel DSP in the light transmitting area TRP. The optical hole OPH may at least partially overlap the light source LS and the photodetector PD.

Figure 25:
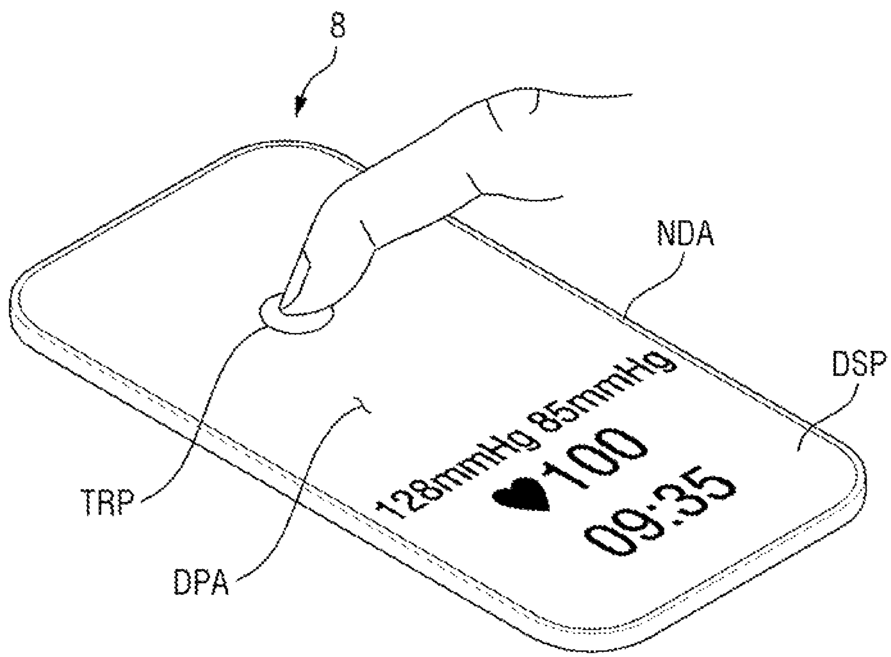
FIG. 25 is a perspective view of an electronic device according to embodiments of the present disclosure.

FIG. 25 is a perspective view of an electronic device 8 according to embodiments of the present disclosure.

FIG. 25 illustrates a case where the electronic device 8 is a smartphone. The electronic device 7 having the cross-sectional structure of FIG. 24 can be easily applied not only to a smart watch as illustrated in FIG. 1, but also to a smartphone as illustrated in FIG. 25.

Referring to FIG. 25, the electronic device 8 includes a light transmitting area TRP. The light transmitting area TRP may include an optical hole as illustrated in FIG. 24. A user may measure blood pressure BP by touching and/or pressing the light transmitting area TRP using a part of his or her body, for example, a finger.

In the current embodiment, the electronic device 8 may have a first blood pressure measurement mode and a second blood pressure measurement mode. The first blood pressure measurement mode may be achieved when a user presses the light transmitting area TRP for a first measurement time. The second blood pressure measurement mode may be achieved when a user touches the light transmitting area TRP for a second measurement time. When the operations of the first blood pressure measurement mode and the second blood pressure measurement mode are performed through the same body part, a blood pressure sensor SN_B and a blood pressure sensor driving unit DRU_SB of the electronic device 8 may measure the blood pressure BP in substantially the same way as described above with reference to FIGS. 5 through 11.

Figure 26:
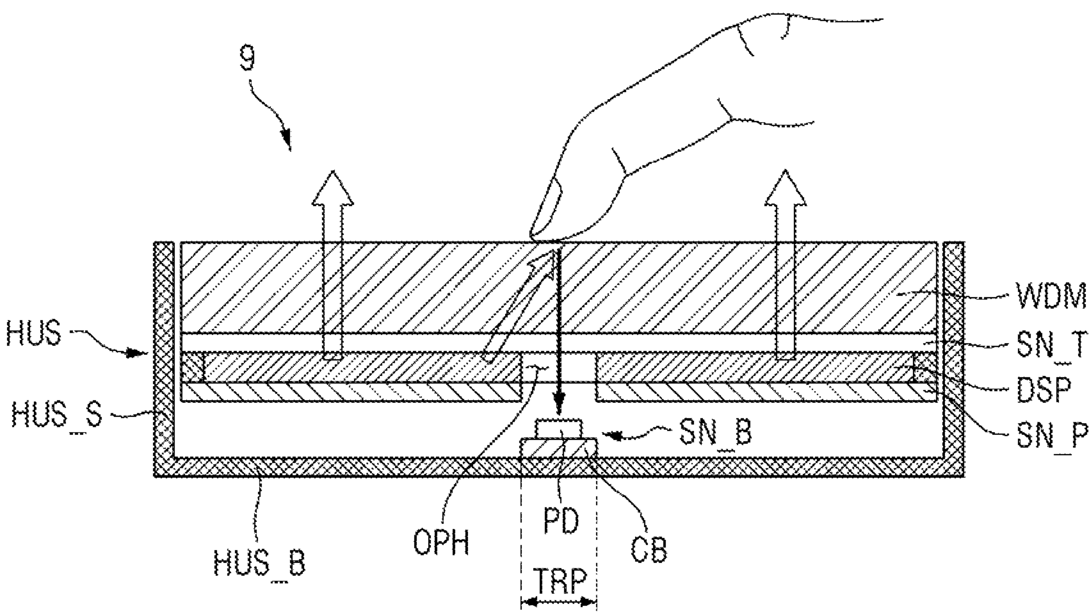
FIG. 26 is a cross-sectional view of an electronic device according to an embodiment of the present disclosure.

FIG. 26 is a cross-sectional view of an electronic device 9 according to an embodiment of the present disclosure.

Referring to FIG. 26, the electronic device 9, according to the current embodiment, is different from that according to the embodiment of FIG. 24 in that a light source LS for a blood pressure sensor SN_B is internalized in a display panel DSP. After examination light emitted from the display panel DSP reaches a part of a user's body, it may be reflected inside the subcutaneous tissue and may pass through a light transmitting area to be incident on a photodetector PD. An example method in which the light source LS for the blood pressure sensor SN_B is internalized in the display panel DSP will be described later through the embodiment of FIG. 28.

Figure 27:
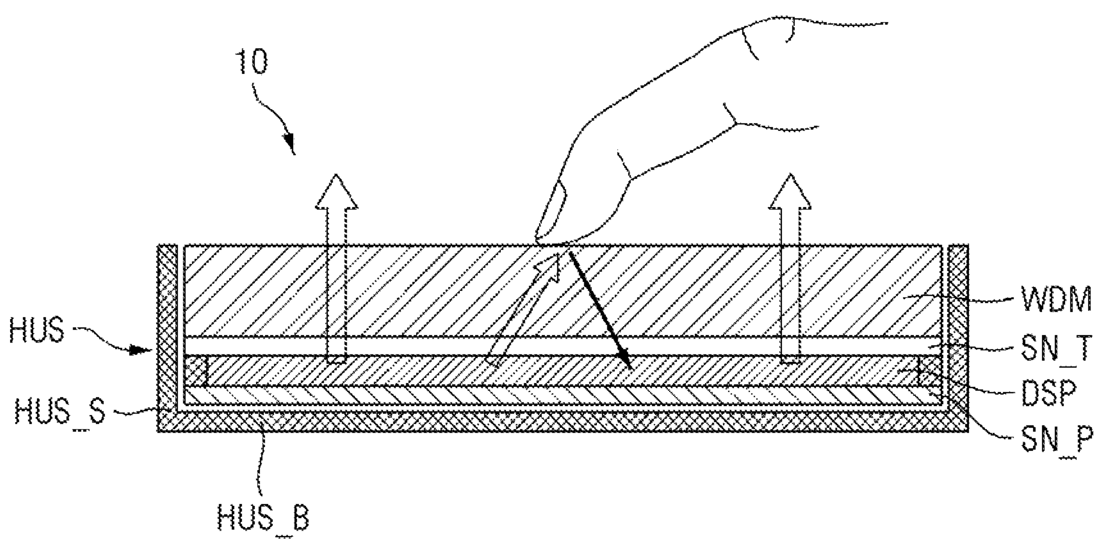
FIG. 27 is a cross-sectional view of an electronic device according to an embodiment of the present disclosure.

FIG. 27 is a cross-sectional view of an electronic device 10 according to an embodiment of the present disclosure.

Referring to FIG. 27, the electronic device 10, according to the current embodiment, is different from that according to the embodiment of FIG. 26 in that not only a light source LS for a blood pressure sensor SN_B but also a photodetector PD are internalized in a display panel DSP. After examination light emitted from the display panel DSP reaches a part of a user's body, it may be reflected inside the subcutaneous tissue and may pass through a light transmitting area to be incident on the photodetector PD inside the display panel DSP. In the current embodiment, since the photodetector PD is located inside the display panel DSP, an optical hole mentioned in FIG. 24 may be omitted or simplified.

Figure 28:
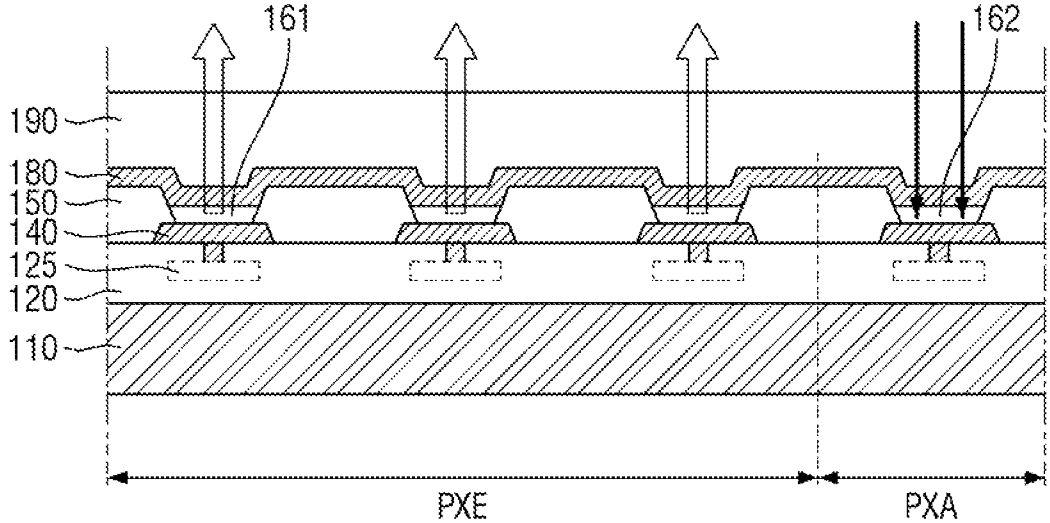
FIG. 28 is an example cross-sectional view of a display panel of the electronic device of FIG. 27.

FIG. 28 is an example cross-sectional view of the display panel DSP of the electronic device 10 of FIG. 27.

Referring to FIG. 28, the display panel DSP may include a plurality of pixels PX. The pixels PX may include light emitting pixels PXE and a light receiving pixel PXA.

For example, a circuit layer 120 is disposed on a substrate 110. The circuit layer 120 may include pixel circuits 125. Each of the pixel circuits 125 may include one or more transistors.

A first electrode 140 may be disposed on the circuit layer 120 for each pixel. A pixel defining layer 150 may be disposed on the first electrode 140 to define each pixel. Active layers 161 and 162 may be disposed on the first electrodes 140 exposed by the pixel defining layer 150. A second electrode 180 may be disposed on the active layers 161 and 162. The first electrode 140 may be a pixel electrode provided for each pixel PX, and the second electrode 180 may be a common electrode connected as one electrode regardless of the pixels PX, but the present disclosure is not necessarily limited thereto. An encapsulation layer 190 may be disposed on the second electrode 180. A touch layer may be further disposed on the encapsulation layer 190.

The active layer 161 of each of the light emitting pixels PXE may include a light emitting layer. The active layer 162 of the light receiving pixel PXA may include a photoelectric conversion layer. The light emitting layers of at least some of the light emitting pixels PXE may each serve as a light source LS for a blood pressure sensor SN_B. For example, light emitted from the light emitting layers of at least some of the light emitting pixels PXE may be used as examination light for measuring blood pressure BP. In addition, the light emitting layers of at least some of the light emitting pixels PXE may each simultaneously perform a screen display function and a function as the light source LS for the blood pressure sensor SN_B. The photoelectric conversion layer of the light receiving pixel PXA may serve as a photodetector PD for the blood pressure sensor SN_B.

The active layers 161 of the light emitting pixels PXE and the active layer 162 of the light receiving pixel PXA may each include a hole injection layer and/or a hole transport layer under the light emitting layer/the photoelectric conversion layer and may further include an electron transport layer and/or an electron injection layer on the light emitting layer/the photoelectric conversion layer. Each of the hole injection layer, the hole transport layer, the electron transport layer, and the electron injection layer may be applied as the same material layer without distinction between the light emitting pixels PXE and the light receiving pixel PXA. Further, each of them may also be provided as a common layer connected as one layer without distinction between the pixels PX.

In the display panel DSP of the current embodiment, the light emitting pixels PXE and the light receiving pixel PXA share a plurality of layers. Therefore, the blood pressure sensor SN_B can be internalized in the display panel DSP in a simple structure.

Figure 29:
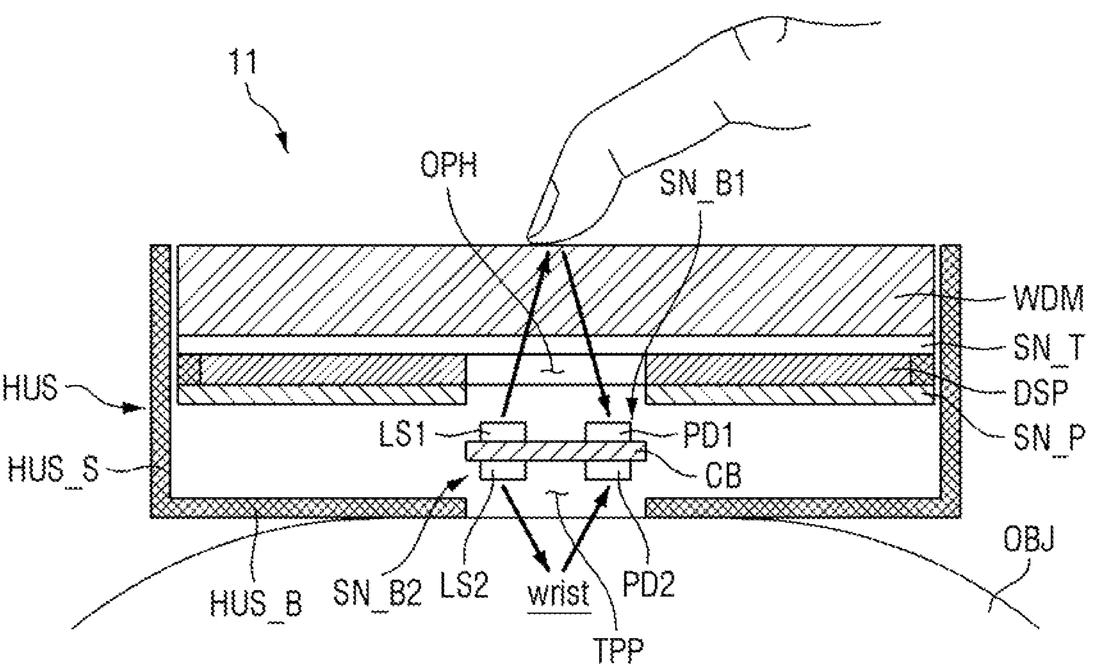
FIG. 29 is a cross-sectional view of an electronic device according to an embodiment of the present disclosure.

FIG. 29 is a cross-sectional view of an electronic device 11 according to an embodiment of the present disclosure.

Referring to FIG. 29, the electronic device 11, according to the current embodiment, is different from that according to the embodiment of FIG. 4 in that blood pressure sensors SN_B include a first blood pressure sensor SN_B1 and a second blood pressure sensor SN_B2.

The first blood pressure sensor SN_B1 includes a first light source LS1 and a first photodetector PD1. The first light source LS1 and the first photodetector PD1 may be placed to face upwardly as in the embodiment of FIG. 24. Therefore, the first blood pressure sensor SN_B1 may measure blood pressure BP of a body part (e.g., a finger) located on a protective member WDM.

The second blood pressure sensor SN_B2 includes a second light source LS2 and a second photodetector PD2. The second light source LS2 and the second photodetector PD2 may be placed to face downward as in the embodiment of FIG. 4. Therefore, the second blood pressure sensor SN_B2 may measure the blood pressure BP of a body part (e.g., the wrist) located under a housing HUS.

In the current embodiment, a first blood pressure measurement mode may be performed by the first blood pressure sensor SN_B1, and a second blood pressure measurement mode may be performed by the second blood pressure sensor SN_B2. Therefore, a body part measured in the first blood pressure measurement mode may be different from a body part measured in the second blood pressure measurement mode. When the body parts measured in the first blood pressure measurement mode and the second blood pressure measurement mode are different as described above, it may be useful to correct a generated pulse wave signal PPG. For example a pulse transit time may be different for each body part, and the shape of the pulse wave signal PPG may change due to this difference. When reference data about the pulse wave signal PPG for each body part or a difference value in pulse wave signal PPG between a reference part (e.g., a finger) and a measured part (e.g., the wrist) is stored in a memory MMR, it may be utilized to correct the pulse wave signal PPG in the second blood pressure measurement mode and measure monitoring blood pressure BP through the corrected pulse wave signal PPG. Correction of the pulse wave signal PPG due to a difference in body part measured may be equally applied not only to the embodiment of FIG. 29 but also to the embodiments described above.

Although the first blood pressure sensor SN_B1 and the second blood pressure sensor SN_B2 share one circuit board CB in FIG. 29, the present disclosure is not necessarily limited thereto. For example, the first light source LS1 and the first photodetector PD1 may be mounted on a first circuit board, and the second light source LS2 and the second photodetector PD2 may be mounted on a second circuit board different from the first circuit board. In addition, although both the first blood pressure sensor SN_B1 and the second blood pressure sensor SN_B2 are disposed inside the housing HUS in FIG. 29, the first blood pressure sensor SN_B1 may be disposed in the housing HUS, and the second blood pressure sensor SN_B2 may also be disposed outside the housing HUS as in the embodiments of FIGS. 22 and 23.

An electronic device, according to an embodiment of the present disclosure, can measure blood pressure in real time with high accuracy.

The various aspects and effects of the present disclosure are not necessarily restricted to the descriptions set forth herein.

In concluding the detailed description, those skilled in the art will appreciate that many variations and modifications can be made to the described embodiments without substantially departing from the principles of the present disclosure.

What is claimed is:

1. An electronic device, comprising:

a housing accommodating a display unit, a pressure sensor unit, and a blood pressure sensor unit, wherein the pressure sensor is configured to receive a pressure applied by a user and a driving unit, wherein the driving unit comprises:

a first calculator circuit configured to calculate a first blood pressure based on a pressure signal received from the pressure sensor unit and a first pulse wave signal received from the blood pressure sensor unit, in a first blood pressure measurement mode of the driving unit; and a second calculator circuit configured to calculate a second blood pressure by comparing a second pulse wave signal received from the blood pressure sensor unit, in a second blood pressure measurement mode of the driving unit, with the first pulse wave signal received in the first blood pressure measurement mode of the driving unit, wherein the first blood pressure is calculated using both the pressure signal received from the pressure sensor unit and the first pulse wave signal received from the blood pressure sensor unit, and the second blood pressure is calculated by comparing the first pulse wave signal received from the blood pressure sensor unit and the second pulse wave signal without the pressure signal.

2. The electronic device of claim 1, wherein the second calculator circuit is further configured to determine the second blood pressure by comparing the first pulse wave signal and the second pulse wave signal in terms of a period, an amplitude, an area, a feature point, and/or a quadratic differential function graph.

3. The electronic device of claim 1, wherein the first pulse wave signal and the second pulse wave signal are pulse wave signals for a same body part of a same person.

4. The electronic device of claim 1, wherein the electronic device is configured to contact a part of a user's body that applies pressure to the electronic device for a first measurement time in the first blood pressure measurement mode and is further configured to contact the part of the user's body for a second measurement time in the second blood pressure measurement mode.

5. The electronic device of claim 4, wherein the first measurement time is within a range of 5 to 80 seconds, and the second measurement time is less than or equal to the first measurement time.

6. The electronic device of claim 1, wherein the first blood pressure is a reference blood pressure, and the second blood pressure is a monitoring blood pressure.

7. The electronic device of claim 1, wherein the blood pressure sensor unit comprises a light source and a photodetector.

8. The electronic device of claim 7, wherein the display unit is configured to display an image in an upward direction, and the light source and the photodetector are disposed facing downward.

9. The electronic device of claim 8, wherein the blood pressure sensor unit is disposed under the display unit, and the housing comprises a light transmitting portion configured to transmit examination light emitted from the light source and reflected from an object.

10. The electronic device of claim 8, wherein the blood pressure sensor unit is disposed on a bottom surface of a bottom portion of the housing.

11. The electronic device of claim 7, wherein the display unit is configured to display an image in an upward direction, the blood pressure sensor unit is disposed under the display unit, and the light source and the photodetector are disposed facing upward.

12. The electronic device of claim 11, wherein the display unit comprises an optical hole at least partially overlapping each of the light source and the photodetector.

13. The electronic device of claim 1, wherein the display unit comprises a light emitting pixel comprising a light emitting layer which emits examination light of the blood pressure sensor unit.

14. The electronic device of claim 13, wherein the display unit further comprises a light receiving pixel comprising a photoelectric conversion layer which receives the examination light.

15. The electronic device of claim 1, wherein the driving unit further comprises a memory configured to store the first pulse wave signal received from the blood pressure sensor unit in the first blood pressure measurement mode as a reference pulse wave signal.

* * * * *